US007662580B2

(12) United States Patent
Georges et al.

(10) Patent No.: US 7,662,580 B2
(45) Date of Patent: Feb. 16, 2010

(54) TISSUE DIAGNOSTICS FOR BREAST CANCER

(75) Inventors: Elias Georges, Laval (CA); Julie Lanthier, Laval (CA); Claudia Boucher, Ile Perrot (CA); Anne-Marie Bonneau, Laval (CA)

(73) Assignee: Aurelium BioPharma Inc., Montreal (CA)

( * ) Notice: Subject to any disclaimer, the term of this patent is extended or adjusted under 35 U.S.C. 154(b) by 289 days.

(21) Appl. No.: 11/595,298

(22) Filed: Nov. 9, 2006

(65) Prior Publication Data

US 2007/0111244 A1    May 17, 2007

Related U.S. Application Data

(60) Provisional application No. 60/735,477, filed on Nov. 10, 2005, provisional application No. 60/802,044, filed on May 18, 2006.

(51) Int. Cl.
*G01N 33/53* (2006.01)
(52) U.S. Cl. .................................... 435/7.23
(58) Field of Classification Search .................. None
See application file for complete search history.

(56) References Cited

U.S. PATENT DOCUMENTS

| 2003/0044859 | A1 | 3/2003 | Henslee et al. | |
| 2007/0134687 | A1* | 6/2007 | Georges et al. | 435/6 |

FOREIGN PATENT DOCUMENTS

| EP | 1946118 | A2 * | 7/2008 |
| JP | 04/151003 | | 5/2004 |
| WO | WO-00/52463 | | 9/2000 |
| WO | WO-02/103320 | | 12/2002 |
| WO | WO-2004/065583 | | 8/2004 |
| WO | WO-2005/028676 | | 3/2005 |
| WO | WO-2005/083440 | | 9/2005 |
| WO | WO-2006/071843 | | 7/2006 |
| WO | WO-2007141595 | A2 * | 12/2007 |

OTHER PUBLICATIONS

Chen et al. "Simultaneous detection of multiple mRNA markers CK19, CEA, c-Met, Her2/neu and hMAM with membrane array, an innovative technique with a great potential for breast cancer diagnosis." *Cancer Letters*. (Aug. 2006) 240 (2): 279-288.
International Search Report, International Patent Application No. PCT/IB2006/004269, mailed Feb. 12, 2008 (5 pgs).
Stathopoulou et al. "Real-Time Quantification of CK-19 mRNA-Positive Cells in Peripheral Blood of Breast Cancer Patients Using the Lightcycler System" *Clinical Cancer Research* (Nov. 2003) 9(14):5145-5151.
Backus John et al. "Identification and characterization of optimal gene expression markers for detection of breast cancer metastasis" Journal of Molecular Diagnostics, vol. 7, No. 3, Aug. 2005 (pp. 327-336).
Chatterjee S K et al. "Cancer biomarkers: knowing the present and predicting the future" Future Oncology, Future Medicine Ltd., London, GB. vol. 1, No. 1, Jan. 1, 2005 (pp. 37-50).
Elliott Bruce E. et al, "The membrane cytoskeletal crosslinker ezrin is required for metastasis of breast carcinoma cells" Breast Cancer Research, vol. 7, No. 3, Mar. 21, 2005 (pp. R365-R373).
Gruenewald Kurt et al. "Mammaglobin gene expression: A superior marker of breast cancer cells in peripheral blood in comparison to epidermal-growth-factor receptor and cytokeratin-19" Laboratory Investigation, vol. 80, No. 7, Jul. 2000. Retrieved from http://breast-cancer-research.com/paperreport/bcr-2000-66689 (1 page).
Imyanitov E N et al., "Mechanisms of breast cancer" Drug Discovery Today: Disease Mechanisms, Elsevier, vol. 1, No. 2, Nov. 1, 2004 (pp. 235-245).
Shen D. et al. "Loss of annexin A1 expression in human breast cancer detected by multiple high-throughput analyses" Biochemical and Biophysical Research communictions, Academic Press Inc., Orlando FL. vol. 326, No. 1. Dec. 31, 2004 (pp. 218-227).
Stathopoulou A et al. "Molecular Detection of Cancer Cells in the Peripheral Blood of Patients with Breast Cancer: Comparison of SK-19, CEA and MASPIN as Detection Markers" Anticancer Research, Helenic Anticancer Institute, Athens, vol. 23, No. 2C, Mar. 1, 2003 (pp. 1883-1890).
Supplementary European Search Report, European Patent Application No. 06851248.2, completed Dec. 19, 2008 (13 pages).
Zhang Dao-Hai et al. "Proteomics of breast cancer: Enhanced expression of cytokeratin 19 in human epidermal growth factor receptor type 2 positive breast tumors" Proteomics, vol. 5, No. 7, May 2005 (pp. 1797-1805).

* cited by examiner

*Primary Examiner*—Misook Yu
(74) *Attorney, Agent, or Firm*—Wilmer, Cutler, Pickering, Hale and Dorr LLP

(57) ABSTRACT

Disclosed are methods for diagnosing breast cancer in a cell sample by detecting an increase in the levels of expression of protein markers in the cell sample as compared to the levels of expression of the same protein markers in a normal, nonneoplastic breast cell sample. Also disclosed is a device for diagnosis of cancer in a cell sample.

6 Claims, 24 Drawing Sheets

FIGURE 17A

| ABP ID | Hormonal | Diagnosis | Stage | Age | Tumor content | Race |
|---|---|---|---|---|---|---|
| BR100 | Pre-menopausal | Infiltrating ductal carcinoma | T1N1M0 | 47 | 100 | Cauc/Russian |
| BR102 | Unknown | Infiltrating ductal breast carcinoma | T2N0M0 | 58 | 100 | Cauc/Russian |
| BR103 | Post-menopausal | Infiltrating ductal breast carcinoma | T2N1M0 | 63 | 100 | Cauc/Russian |
| BR104 | Post-menopausal | Infiltrating ductal carcinoma | T2N1M0 | 62 | 100 | Cauc/Russian |
| BR105 | nd | Infiltrating duct carcinoma of the breast | T2N1M0 | 48 | 100 | Cauc/Russian |
| BR106 | Pre-menopausal | Infiltrating ductal carcinoma | T2N0M0 | 45 | 100 | Cauc/Tartar |
| BR111 | Pre-menopausal | Infiltrating ductal carcinoma | T2N1M0 | 39 | 80 | Cauc/Russian |
| BR112 | Pre-menopausal | Invasive ductal carcinoma of breast | T2N0M0 | 46 | 70 | Asian |
| BR113 | Pre-menopausal | Infiltrating ductal breast carcinoma | T2N1M0 | 47 | 70 | Cauc/Russian |
| BR114 | Pre-menopausal | Infiltrating ductal breast carcinoma | T1N0M0 | 44 | 70 | Cauc/Russian |
| BR116 | Pre-menopausal | Invasive ductal carcinoma of breast | T1N1M0 | 39 | 75 | Asian |
| BR117 | Pre-menopausal | Invasive ductal carcinoma of right Breast | T2N1M0 | 40 | 75 | Asian |
| BR121 | Pre-menopausal | Infiltrating duct carcinoma of right Breast | T2N0M0 | 43 | 80 | Asian/Bashkir |
| BR122 | Pre-menopausal | Infiltrating ductal breast carcinoma | T1N1M0 | 47 | 70 | Cauc/Russian |
| BR123 | Pre-menopausal | Invasive ductal carcinoma | T3N0M0 | 29 | 70 | Asian |
| BR124 | Pre-menopausal | Infiltrating Ductal Carcinoma | T2N0M0 | 37 | 70 | Cauc |
| BR125 | Pre-menopausal | Infiltrating ductal carcinoma | T2N0M0 | 37 | 80 | Cauc/Tartarian |
| BR126 | Pre-menopausal | Infiltrating ducatal carcinoma | T2N1M0 | 55 | 70 | Cauc/Russian |
| BR128 | Post-menopausal | Invasive ductal carcinoma | T1N0M0 | 51 | 80 | Asian |
| BR129 | Post-menopausal | Invasive ductal carcinoma of breast | T3N2M0 | 54 | 90 | Asian |
| BR130 | Post-menopausal | Invasive ductal carcinoma of breast | T2N0M0 | 67 | 80 | Asian |
| BR131 | Post-menopausal | Infiltrating ductal carcinoma | T2N1M0 | 45 | 80 | Cauc/Russian |
| BR132 | Post-menopausal | Infiltrating duct carcinoma of Breast | T4N3M0 | 54 | 80 | Cauc/Russian |
| BR133 | Post-menopausal | Infiltrating duct carcinoma of Breast | T2N1M0 | 62 | 75 | Cauc/Russian |
| BR134 | Post-menopausal | Infiltrating duct carcinoma of Breast | T2N0M0 | 54 | 80 | Cauc/Russian |
| BR135 | Post-menopausal | Invasive ductal carcinoma of left breast | T2pN1M0 | 54 | 80 | Asian/Chinese |
| BR136 | Post-menopausal | Infiltrating duct carcinoma of Breast | T2N0M0 | 64 | 70 | Cauc/Russian |
| BR137 | Post-menopausal | Infiltrating ductal breast carcinoma | T2N0M0 | 57 | 90 | Cauc/Russian |
| BR138 | Post-menopausal | Infiltrating ductal breast carcinoma | T2N0M0 | 66 | 70 | Cauc/Russian |
| BR139 | Post-menopausal | Infiltrating ductal breast carcinoma | T2N1M0 | 54 | 70 | Cauc |
| BR140 | Post-menopausal | Infiltrating ductal breast carcinoma | T2N1M0 | 53 | 70 | Cauc/Russian |
| BR143 | Post-menopausal | Infiltrating duct carcinoma of left breast | T3N3M0 | 78 | 75 | Cauc/Russian |
| BR144 | Post-menopausal | Infiltrating duct carcinoma | T2N1M0 | 54 | 80 | Cauc/Russian |
| BR145 | Post-menopausal | Infiltrating duct carcinoma | T4N1M0 | 56 | 80 | Cauc/Russian |
| BR146 | Post-menopausal | Infiltrating duct carcinoma of the left breast | T2N1M0 | 54 | 70 | Cauc/Russian |
| BR148 | Post-menopausal | Invasive ductal carcinoma | T2N0M0 | 67 | 70 | Asian |
| BR149 | Post-menopausal | Infiltrating ductal cacinoma | T2N0M0 | 55 | 90 | Cauc/Russian |
| BR151 | Post-menopausal | Infiltrating ductal carcinoma | T4N1M0 | 55 | 80 | Cauc |
| BR152 | Post-menopausal | Infiltrating ducal carcinoma | T3N2M0 | nd | 70 | Cauc |
| BR153 | Post-menopausal | Infiltrating ductal carcinoma | T2N0M0 | 55 | 70 | Cauc/Russian |
| BR154 | Post-menopausal | Infiltrating ductal carcinoma | T3N0M0 | 54 | 70 | Cauc/Russian |
| BR155 | Post-menopausal | Infiltrating ductal carcinoma | T4N1M0 | 70 | 70 | Cauc/Russian |
| BR156 | Post-menopausal | Infiltrating ductal carcinoma | T1N0M0 | 67 | 70 | Cauc/Russian |
| BR158 | Pre-menopausal | Infiltrating duct breast carcinoma | T1N0M0 | 46 | 75 | Cauc/Russian |
| BR159 | Pre-menopausal | Invasive ductal carcinoma of breast | T1N1M0 | 39 | 70 | Asian/Chinese |
| BR160 | Post-menopausal | Infiltrating ductal carcinoma | T2N0M0 | 62 | 70 | Cauc |
| BR161 | Pre-menopausal | Invasive ductal carcinoma of breast | T2N1M0 | 29 | 80 | Asian |
| BR162 | Post-menopausal | Infiltrating ductal carcinoma | T2N0M0 | 68 | 70 | Cauc/Russian |
| BR163 | Pre-menopausal | Invasive ductal carcinoma of breast | T2N1M0 | 48 | 80 | Asian |
| BR165 | Post-menopausal | Infiltrating ductal carcinoma | T4N1M0 | 74 | 70 | Cauc/Russian |
| BR166 | Post-menopausal | Infiltrating ductal carcinoma | T1N1M0 | 56 | 80 | Cauc/Russian |
| BR167 | Post-menopausal | Infiltrating ductal carcinoma | T2N1M0 | 77 | 70 | Cauc/Russian |
| BR168 | Pre-menopausal | Invasive ductal carcinoma of breast | T1N0M0 | 47 | 75 | Asian/Chinese |
| BR169 | nd | Infiltrating ductal carcinoma | T2N0M0 | 50 | 70 | Cauc/Russian |
| BR170 | Pre-menopausal | Invasive ductal carcinoma of breast | T2N1M0 | 38 | 80 | Asian |
| BR171 | nd | Infiltrating ductal carcinoma | T2N1M0 | 51 | 70 | Cauc/Russian |
| BR172 | Post-menopausal | Infiltrating ductal carcinoma | T2N0M1 | 65 | 70 | Cauc/Russian |
| BR173 | Pre-menopausal | Infiltrating ductal carcinoma | T2N0M1 | 44 | 80 | Cauc |
| BR174 | Post-menopausal | Infiltrating ductal carcinoma | T2N0M0 | 61 | 70 | Cauc/Russian |
| BR175 | Post-menopausal | Infiltrating ductal carcinoma | T2N0M0 | 87 | 95 | Cauc/Russian |
| BR176 | Pre-menopausal | Invasive ductal carcinoma of breast | T2pNbiM0 | 27 | 80 | Asian |

FIGURE 17B

| ABP ID | Menauposal status | Age | Race |
|---|---|---|---|
| BR403 | Pre-menopausal | 26 | Cauc |
| BR423 | Pre-menopausal | 19 | nd |
| BR432 | Pre-menopausal | 15 | nd |
| BR433 | Pre-menopausal | 15 | nd |
| BR453 | Post-menopausal | 89 | Cauc |
| BR457 | Pre-menopausal | 28 | Cauc |
| BR500 | Pre-menopausal | 46 | Cauc |
| BR501 | Pre-menopausal | 43 | Asian/Bashkirian |
| BR502 | Pre-menopausal | 48 | Cauc/Russian |
| BR503 | Pre-menopausal | 42 | Cauc |
| BR505 | Pre-menopausal | 46 | Cauc |
| BR506 | Pre-menopausal | 43 | Cauc/Russian |
| BR507 | Pre-menopausal | 36 | Cauc/Russian |
| BR508 | nd | 52 | Cauc/Russian |
| BR509 | Pre-menopausal | 34 | Cauc/Russian |
| BR510 | nd | 46 | Asian |
| BR511 | Pre-menopausal | 34 | Other |
| BR512 | Pre-menopausal | 48 | Cauc/Russian |
| BR516 | Pre-menopausal | 43 | Cauc/Russian |
| BR525 | Pre-menopausal | 41 | Cauc/Russian |
| BR526 | Pre-menopausal | 37 | Cauc/Russian |
| BR529 | nd | 52 | Cauc/Russian |
| BR530 | Pre-menopausal | 36 | Cauc |
| BR531 | nd | 51 | Cauc/Russian |
| BR550 | Pre-menopausal | 43 | Cauc/Russian |
| BR552 | Post-menopausal | 57 | Cauc |

TISSUE DIAGNOSTICS FOR BREAST CANCER

This application claims the benefit of priority to U.S. Provisional Application No. 60/735,477, filed Nov. 10, 2005 and to U.S. Provisional Application No. 60/802,044, filed May 18, 2006, the specifications of which are incorporated by reference in their entirety.

FIELD OF THE INVENTION

The present invention relates generally to the field of medicine. More specifically, the invention pertains to methods and devices for detecting the development of cancer in cell samples isolated from a subject.

BACKGROUND OF THE INVENTION

Cancer is one of the deadliest illnesses in the United States. It accounts for nearly 600,000 deaths annually in the United States, and costs billions of dollars for those who suffer from the disease. This disease is in fact a diverse group of disorders, which can originate in almost any tissue of the body. In addition, cancers may be generated by multiple mechanisms including pathogenic infections, mutations, and environmental insults (see, e.g., Pratt et al. (2005) Hum Pathol. 36(8): 861-70). The variety of cancer types and mechanisms of tumorigenesis add to the difficulty associated with treating a tumor, increasing the risk posed by the cancer to the patient's life and wellbeing.

Cancers manifest abnormal growth and the ability to move from an original site of growth to other tissues in the body (hereinafter termed "metastasis"), unlike most non-cancerous cells. These clinical manifestations are therefore used to diagnose cancer because they are applicable to all cancers. Additionally, a cancer diagnosis is made based on identifying cancer cells by their gross pathology through histological and microscopic inspection of the cells. Although the gross pathology of the cells can provide accurate diagnoses of the cells, the techniques used for such analysis are hampered by the time necessary to process the tissues and the skill of the technician analyzing the samples. These methodologies can lead to unnecessary delay in treating a growing tumor, thereby increasing the likelihood that a benign tumor will acquire metastatic characteristics. It is thus necessary to accurately diagnose potentially cancerous growths as quickly as possible to avoid the development of a potentially life threatening illness.

One potential method of increasing the speed and accuracy of cancer diagnoses is the examination of genes as markers for neoplastic potential. Recent advances in molecular biology have identified genes involved in cell cycle control, apoptosis, and metabolic regulation (see, e.g., Isoldi et al. (2005) Mini Rev. Med. Chem. 5(7): 685-95). Mutations in many of these genes have also been shown to increase the likelihood that a normal cell will progress to a malignant state (see, e.g., Soejima et al. (2005) Biochem. Cell Biol. 83(4): 429-37). For example, mutations in p53, which is a well-known tumor suppressor gene, have been associated with aberrant cell growth leading to neoplastic potential (see Li et al. (2005) World J. Gastroenterol. 11(19): 2998-3001). Many mutations can affect the levels of expression of certain genes in the neoplastic cells as compared to normal cells.

Typically, a gene will affect the phenotype of the cell through its expression at the protein level. Mutations in the coding sequence of the gene can alter its protein product in such a way that the protein does not perform its intended function appropriately. Some mutations, however, affect the levels of protein expressed in the cell without altering the functionality of the protein itself. Such mutations directly affect the phenotype of a cell by changing the delicate balance of protein expression in a cell. Therefore, an alteration in a gene's overall activity can be measured by determining the level of expression of the protein product of the gene in a cell.

There remains a need to identify an accurate and rapid means for diagnosing cancer in patients. Treatment efficacy would be improved by more efficient diagnoses of tissue samples. Furthermore, rapid diagnoses of cancerous tissues would allow clinicians to treat potential tumors prior to the metastasis of the cancer to other tissues of the body. Finally, a test that did not rely upon a particular technician's skill at identifying abnormal histological characteristics would improve the reliability of cancer diagnoses. There is, therefore, a need for new methods of diagnoses for cancer that are accurate, fast, and relatively easy to interpret.

SUMMARY OF THE INVENTION

The present invention is based in part upon the discovery that differential expression of certain genes at the protein level occurs when a cell progresses to a neoplastic state. These protein expression patterns are therefore diagnostic for the presence of cancer in a cell sample. This discovery has been exploited to provide an invention that uses such patterns of expression to diagnose the presence of neoplastic cells in the cell sample.

In one aspect, the invention provides a method of diagnosing cancer in a subject. The method comprises the step of selecting at least one protein marker from cytokeratin 19, cathepsin D, ezrin, A-CRABP II, slc9a3rl, and HER-2. Once the protein marker is selected, a level of expression of the selected protein markers in a sample isolated from the subject (e.g., biological fluid sample or cell sample) is detected by contacting protein-targeting agents that binds to the protein markers isolated from the sample. The level of expression of the selected protein marker(s) in the sample is compared to a level of expression of the same protein marker(s) detected in a control sample of the same tissue type as the sample. The presence of cancer is indicated if the level of expression of one or more protein markers in the sample is greater than the level of expression for the same protein markers in the control sample of the same tissue type.

In another aspect, the invention provides a method of diagnosing breast cancer in a subject. The method comprises the step of selecting at least two protein markers from cytokeratin 19, cathepsin D, ezrin, A-CRABP II, slc9a3rl, and HER-2. Once the protein markers are selected, a level of expression of the selected protein marker(s) in a potentially cancerous breast cell sample is detected by contacting targeting agent, or agents, that binds to the protein marker(s) isolated from the cell sample. The level of expression of the selected protein marker(s) in the potentially cancerous breast cell sample is compared to a level of expression of the same protein markers detected in a normal control breast cell sample. The presence of breast cancer is indicated if the level of expression of the selected protein marker(s) in the breast cell sample is greater than the level of expression for the same protein marker(s) in the normal breast control cell sample.

In certain embodiments, at least two protein markers are selected, and an increased level of expression of at least one of the selected protein markers in the potentially cancerous breast cell sample compared to their level of expression in the normal breast control cell sample indicates the presence of breast cancer. In further embodiments, at least three protein markers are selected, and an increased level of expression of at least two of the selected protein markers in a potentially cancerous breast cell sample compared to their level of expression in the normal breast cell sample indicates the presence of breast cancer. In still other embodiments, at least four protein markers are selected, and an increased level of expression of at least three of the selected protein markers in the breast cell sample compared to their level of expression in the normal breast control cell sample indicates the presence of breast cancer. In particular embodiments, the selected protein marker comprises cytokeratin 19, ezrin, cathepsin D, A-CRABP II, and HER-2. In certain embodiments, the protein targeting agents are selected from the group consisting of ligands, inhibitors, peptidomimetic compounds, peptides, proteins, antibodies, antigen-binding fragments, and combinations thereof. In other embodiments, the level of expression of protein markers is detected by protein capture probes attached to a solid support.

In particular embodiments, the breast cancer is a breast adenocarcinoma, infiltrating ductal carcinoma, breast carcinoma, serous adenocarcinoma, clear cell adenocarcinoma, endometrioid carcinoma, and mucinous adenocarcinoma. In certain embodiments, the subject is a human. In other embodiments, the presence of cancer is indicated if in the potentially cancerous breast cell sample the level of expression of at least one of the selected protein markers is increased or decreased by at least two times when compared to the level of expression of the same protein marker in the normal breast control cell sample.

In further embodiments, the protein markers are from the group consisting of cytokeratin 19, ezrin, cathepsin D, A-CRABP II, and slc9a3rl. In particular embodiments, the presence of cancer is indicated if the level of expression in the potentially cancerous breast cell sample of at least one of the selected protein markers is at least two times the level of expression of the same protein markers in the normal breast control cell sample.

In some embodiments, the protein markers are cytokeratin 19, ezrin, cathepsin D, A-CRABP II, slc9a3rl, and HER-2. In a particular embodiment, the presence of cancer is indicated if the level of expression in the potentially cancerous breast cell sample of at least one of the selected protein markers is increased or decreased by at least three times when compared to the level of expression of the same protein markers in the normal breast control cell sample.

In some embodiments, the step of comparing the level of expression of the selected protein markers further comprises using a class prediction algorithm to differentiate the level of expression of the selected protein markers in the cell sample from the level of expression of the same protein markers in the normal cell sample. In certain embodiments, the level of expression of protein markers is determined using protein microarray, ELISA, Western blotting, and dipstick assays. In certain embodiments, the detection means is selected from the group consisting of fluorophores, chemical dyes, radiolabels, chemiluminescent compounds, colorimetric enzymatic reactions, chemiluminescent enzymatic reactions, magnetic compounds, and paramagnetic compounds.

In another aspect, the invention provides a method of diagnosing breast cancer in a subject. The method comprises the step of selecting at least two protein markers from cytokeratin 19, cathepsin D, ezrin, A-CRABP II, slc9a3rl, and HER-2. Once the protein markers are selected, a level of expression of the selected protein marker(s) in a biological fluid sample isolated from the patient is detected by contacting targeting agent, or agents, that binds to the protein marker(s) isolated from the cell sample. The level of expression of the selected protein marker(s) in the biological fluid sample is compared to a level of expression of the same protein markers detected in a control sample. The presence of breast cancer is indicated if the level of expression of the selected protein marker(s) in the biological fluid sample is greater than the level of expression for the same protein marker(s) in the control sample.

In certain embodiments, at least two protein markers are selected, and an increased level of expression of at least one of the selected protein markers in the biological fluid sample compared to their level of expression in the control sample indicates the presence of breast cancer. In further embodiments, at least three protein markers are selected, and an increased level of expression of at least two of the selected protein markers in the biological fluid sample compared to their level of expression in the control sample indicates the presence of breast cancer. In still other embodiments, at least four protein markers are selected, and an increased level of expression of at least three of the selected protein markers in the biological fluid sample compared to their level of expression in the control sample indicates the presence of breast cancer. In particular embodiments, the selected protein marker comprises cytokeratin 19, ezrin, cathepsin D, A-CRABP II, and HER-2. In certain embodiments, the protein targeting agents are selected from the group consisting of ligands, inhibitors, peptidomimetic compounds, peptides, proteins, antibodies, antigen-binding fragments, and combinations thereof. In other embodiments, the level of expression of protein markers is detected by protein capture probes attached to a solid support.

In particular embodiments, the breast cancer is a breast adenocarcinoma, infiltrating ductal carcinoma, breast carcinoma, serous adenocarcinoma, clear cell adenocarcinoma, endometrioid carcinoma, and mucinous adenocarcinoma. In certain embodiments, the subject is a human. In some embodiments, the biological fluid sample includes blood, bile, serum, sweat, urine, mucosal secretions, saliva, seminal fluid, cerebrospinal fluid, tears, and sebaceous secretions. In certain embodiments, the biological fluid sample is blood or serum. In other embodiments, the presence of cancer is indicated if in the biological fluid sample the level of expression of at least one of the selected protein markers is increased or decreased by at least two times when compared to the level of expression of the same protein marker in the control sample. In other embodiments, the level of expression of the selected protein markers is increased or decreased by at least 1.1 to 1.5 times when compared to the level of expression of the same protein marker in the control sample.

In further embodiments, the protein markers are from the group consisting of cytokeratin 19, ezrin, cathepsin D, A-CRABP II, and slc9a3rl. In particular embodiments, the presence of cancer is indicated if the level of expression in the biological fluid sample of at least one of the selected protein markers is at least two times the level of expression of the same protein markers in the control sample. In other embodiments, the level of expression of the selected protein markers is increased or decreased by at least 1.1 to 1.5 times when compared to the level of expression of the same protein marker in the control sample.

In some embodiments, the protein markers are cytokeratin 19, ezrin, cathepsin D, A-CRABP II, slc9a3rl, and HER-2. In a particular embodiment, the presence of cancer is indicated if the level of expression in the biological fluid sample of at least one of the selected protein markers is increased or decreased by at least three times when compared to the level of expression of the same protein markers in the control sample. In other embodiments, the level of expression of the selected protein markers is increased or decreased by at least 1.1 to 1.5 times when compared to the level of expression of the same protein marker in the control sample.

In some embodiments, the step of comparing the level of expression of the selected protein markers further comprises using a class prediction algorithm to differentiate the level of expression of the selected protein markers in the biological fluid sample from the level of expression of the same protein markers in the control sample. In certain embodiments, the level of expression of protein markers is determined using protein microarray, ELISA, Western blotting, and dipstick assays. In certain embodiments, the detection means is selected from the group consisting of fluorophores, chemical dyes, radiolabels, chemiluminescent compounds, colorimetric enzymatic reactions, chemiluminescent enzymatic reactions, magnetic compounds, and paramagnetic compounds.

In another aspect, the invention provides a focused microarray for diagnosing a neoplasm. The focused microarray comprises a first set of protein capture probes that bind specifically to a protein marker from the group consisting of cytokeratin 19, ezrin, cathepsin D, A-CRABP II, slc9a3rl, and HER-2. The first set comprises at least two different protein capture probes. The focused microarray further contains a second set of protein capture probes, each of which binds to an endogenous housekeeping protein. Also, a solid support is provided to which the first and second set of protein capture probes are attached at predetermined positions.

In certain embodiments, the first set of capture probes binds to at least three of the protein markers from the group consisting of cytokeratin 19, ezrin, cathepsin D, A-CRABP II, slc9a3rl, and HER-2. In other embodiments, the first set of capture probes binds to at least four of the protein markers from the group consisting of cytokeratin 19, ezrin, cathepsin D, A-CRABP II, slc9a3rl, and HER-2. In still other embodiments, the first set of capture probes binds to the protein markers consisting of cytokeratin 19, ezrin, cathepsin D, A-CRABP II, slc9a3rl, and HER-2. In some embodiments, the protein capture probes are from the group consisting of ligands, inhibitors, peptidomimetic compounds, peptides, proteins, antibodies, antigen-binding fragments of antibodies, and combinations thereof. In other embodiments, the neoplasm diagnosed is a breast adenocarcinoma, infiltrating ductal carcinoma, breast carcinoma, serous adenocarcinoma, clear cell adenocarcinoma, endometrioid carcinoma, and mucinous adenocarcinoma.

In yet another aspect, the invention provides a kit for diagnosing cancer in a subject. The kit provides a first set of probes for the detection of one or more protein markers selected from the group consisting of cytokeratin 19, ezrin, cathepsin D, A-CRABP II, slc9a3rl, and HER-2. The kit also provides a second set of probes for the detection of one or more endogenous housekeeping proteins. Furthermore, the kit contains a detection means for identifying a probe binding to a target protein marker.

In certain embodiments, the second set of protein targeting agents is specific for protein markers that do not vary statistically significantly in their level of expression between potentially cancerous cell samples and normal control cell samples.

In certain embodiments, the detection means is selected from the group consisting of fluorophores, chemical dyes, radiolabels, chemiluminescent compounds, colorimetric enzymatic reactions, chemiluminescent enzymatic reactions, magnetic compounds, and paramagnetic compounds. In particular embodiments, the first and second sets of protein targeting agents are attached to a solid support at predetermined positions. In more particular embodiments, the cancer being detected using the kit is a breast adenocarcinoma, a breast epithelial adenocarcinoma, or a mucinous carcinoma.

In another aspect, the invention provides a method of diagnosing breast cancer in a subject. The method comprises selecting the protein markers cytokeratin 19, ezrin, cathepsin D, A-CRABP II, slc9a3rl, and HER-2. Next, a level of expression for the protein markers is detected in a potentially cancerous breast cell sample by binding targeting agents with the protein markers isolated from the cell sample. The level of expression of the same protein markers is detected in a normal breast control cell sample by binding targeting agents with the protein markers isolated from the normal breast control cell sample. The level of expression of the protein markers in a potentially cancerous breast cell sample is compared to the level of expression of the same protein markers in the normal breast control cell sample. The presence of breast cancer is indicated if the level of expression of the protein markers in the potentially cancerous breast cell sample is greater than the level of expression of the same protein markers in the breast normal control cell sample.

BRIEF DESCRIPTION OF THE FIGURES

The foregoing and other objects of the present invention, the various features thereof, as well as the invention itself may be more fully understood from the following description, when read together with the accompanying drawings in which:

FIG. 17A is a tabular representation showing the individual profiles for patients donating tumor tissue samples.

FIG. 17B is a tabular representation showing the individual profiles for normal individuals donating normal breast tissue.

DETAILED DESCRIPTION OF THE INVENTION

Figure 1A:
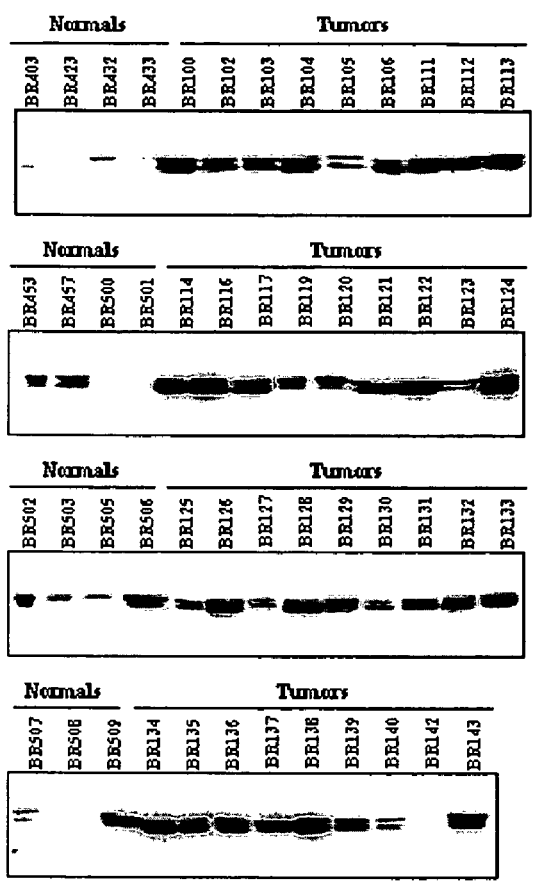
FIG. 1A is a photographic representation of 8 different immunoblots probed with anti-cytokeratin 19 antibody that shows the level of expression of cytokeratin 19 in tissue samples from normal subjects ("Normals") and breast cancer patients ("Tumors"), normal and tumor samples are identified by the BR number provided.
Figure 1A:
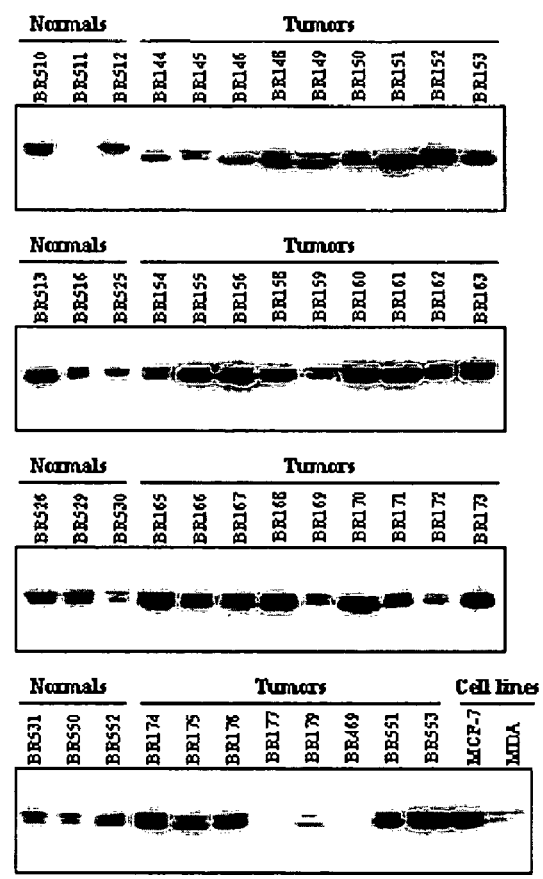

The patent and scientific literature referred to herein establishes knowledge that is available to those of skill in the art. The issued US patents, allowed applications, published foreign applications, and references, including GenBank database sequences, that are cited herein are hereby incorporated by reference to the same extent as if each was specifically and individually indicated to be incorporated by reference.

1.1. General

The present invention provides, in part, methods and kits for diagnosing, detecting, or screening a cell sample for tumorigenic potential and neoplastic characteristics such as aberrant growth. The invention also allows for the improved clinical management of tumors by providing a device that detects the expression level of genes identified as markers for cancer.

Typically, a gene will affect the phenotype of the cell through its expression at the protein level. Mutations in the coding sequence of the gene can alter its protein product in such a way that the protein does not perform its intended function appropriately. Some mutations, however, affect the levels of protein expressed in the cell without altering the functionality of the protein, itself. Such mutations directly affect the phenotype of a cell by changing the delicate balance of protein expression in a cell. Therefore, an alteration in a gene's overall activity can be measured by determining the level of expression of the protein product of the gene in a cell.

Accordingly, one aspect of the invention provides a method for diagnosing cancer in a cell. The method utilizes protein-targeting agents to identify proteins in a potentially cancerous cell sample or a potentially cancerous serum sample. Increased levels of expression of particular protein markers in a cell or serum sample indicate the presence of a neoplasm.

As used herein, the term "protein-targeting agent" means a molecule capable of binding or interacting with a protein or a portion of a protein. Such binding or interactions can include ionic bonds, van der Waals interactions, London forces, covalent bonds, and hydrogen bonds. The target protein can be bound in a receptor binding pocket, on its surface, or any other portion of the protein that is accessible to binding or interactions with a molecule. Protein-targeting agents include, but are not limited to, proteins, peptides, ligands, peptidomimetic compounds, inhibitors, organic molecules, aptamers, or combinations thereof.

As used herein, the term "tumorigenic potential" means capable of giving rise to either benign or malignant tumors. Tumorigenic potential may occur through genetic mechanisms such as mutation or through infection with vectors such as viruses and bacteria.

The term "cancer" refers herein to a disease condition in which a tissue or cells exhibit aberrant, uncontrolled growth and/or lack of growth inhibition. A cancer can be a single cell or, alternatively, a tumor composed of hyperplastic cells. In addition, cancers can be malignant and metastatic, spreading from an original tumor site to other tissues in the body. In contrast, some cancers are localized to a single tissue of the body.

As used herein, a "cancer cell" is a cell that shows aberrant cell growth, such as increased, uncontrolled cell proliferation and/or lack of contact inhibition. A cancer cell can be a hyperplastic cell, a cell from a cell line that shows a lack of contact inhibition when grown in vitro, or a cancer cell that is capable of metastasis in vivo. In addition, cancer cells include cells isolated from tumor or tumors. As used herein, a "tumor" is a collection of cells that exhibit the characteristics of cancer cells. Non-limiting examples of cancer cells include melanoma, ovarian cancer, ovarian cancer, prostate cancer, sarcoma, leukemic retinoblastoma, hepatoma, myeloma, glioma, mesothelioma, carcinoma, leukemia, lymphoma, Hodgkin lymphoma, Non-Hodgkin lymphoma, promyelocytic leukemia, lymphoblastoma, and thymoma, and lymphoma cells, melanoma cells, sarcoma cells, leukemia cells, retinoblastoma cells, hepatoma cells, myeloma cells, glioma cells, mesothelioma cells, a breast adenocarcinoma, infiltrating ductal carcinoma, breast carcinoma, serous adenocarcinoma, clear cell adenocarcinoma, endometrioid carcinoma, and mucinous adenocarcinoma, and carcinoma cells.

As used herein, the term "inhibitor" means a compound that prevents a biomolecule, e.g., a protein, nucleic acid, or ribozyme, from completing or initiating a reaction. An inhibitor can inhibit a reaction by competitive, uncompetitive, or non-competitive means. Exemplary inhibitors include, but are not limited to, nucleic acids, proteins, small molecules, chemicals, peptides, peptidomimetic compounds, and analogs that mimic the binding site of an enzyme. In some embodiments, the inhibitor can be nucleic acid molecules including, but not limited to, siRNA that reduce the amount of functional protein in a cell.

The term "protein markers" as used herein means any protein, peptide, polypeptides, group of peptides, or proteins expressed from a gene, whether chromosomal, extrachromosomal, endogenous, or exogenous, which may produce a phenotype in the cancer cell or the organism. As used herein, "gene" means any deoxyribonucleic acid sequence capable of being translated into a protein or peptide sequence. The gene is a DNA sequence that may be transcribed into an mRNA and then translated into a peptide or protein sequence. Extrachromosomal sources of nucleic acid sequences can include double-strand DNA viral genomes, single-stranded DNA viral genomes, double-stranded RNA viral genomes, single-stranded RNA viral genomes, bacterial DNA, mitochondrial genomic DNA, cDNA or any other foreign source of nucleic acid that is capable of generating a gene product.

Protein markers can have any structure or configuration, and can be in any location within a cell, on the cell surface. Protein markers can also be secreted from the cell into an extracellular matrix or directly into the blood or other biological fluid. Protein markers can be a single polypeptide chain or peptide fragments of a polypeptide. Moreover, protein markers can also be combinations of nucleic acids and polypeptides as in the case of a ribosome. Protein markers can have any secondary structure combination, any tertiary structure, and come in quaternary structures as well.

As used herein, the term "normal control cell sample" refers to a cell or group of cells that is exhibiting common characteristics for the particular cell type from which the cell or group of cells was isolated. A normal cell sample does not exhibit tumorigenic potential, metastatic potential, or aberrant growth in vivo or in vitro. A normal control cell sample can be isolated from tissues in a subject that is not suffering from cancer. It may not be necessary to isolate a normal control cell sample each time a cell sample is tested for cancer as long as the nucleic acids isolated from the normal control cell sample allow for probing against the focused microarray during the testing procedure.

In another aspect, the invention provides methods for diagnosing cancer in a cell sample using a protein microarray. The methods can be practiced using a microarray composed of capture probes affixed to a derivatized solid support such as, but not limited to, glass, nylon, metal alloy, or silicon. Non-limiting examples of derivatizing substances include aldehydes, gelatin-based substrates, epoxies, poly-lysine, amines and silanes. Techniques for applying these substances to solid surfaces are well known in the art. In useful embodiments, the solid support can be comprised of nylon.

For purposes of the invention, the term "capture probe" is intended to mean any agent capable of binding a gene product in a complex cell sample. Capture probes can be disposed on the derivatized solid support utilizing methods practiced by those of ordinary skill in the art through a process called "printing" (see, e.g., Schena et. al., (1995) *Science,* 270(5235): 467-470). The term "printing", as used herein, refers to the placement of spots onto the solid support in such close proximity as to allow a maximum number of spots to be disposed onto a solid support. The printing process can be carried out by, e.g., a robotic printer. The VersArray CHIP Writer Prosystem (BioRad Laboratories) using Stealth Micro Spotting Pins (Telechem International, Inc, Sunnyvale, Calif.) is a non-limiting example of a chip-printing device that can be used to produce the focused microarray for this aspect. In certain embodiments, capture probes are antibodies or any other molecule, which are attached to a solid support at predetermined positions, capable of binding a protein (herein termed "protein capture probes").

In some embodiments, the levels of expression of the protein markers in the potentially cancerous cell sample are compared to the levels of expression of the protein markers in a normal control cell sample of the same tissue type as the cell sample. If the expression of at least one protein marker in the cell sample is greater than the expression of the protein marker or genes in the normal control cell sample, then cancer is indicated. In some embodiments, the potentially cancerous cell sample is tumorigenic if the level of expression of at least two or more of the plurality of protein markers in the cell sample is greater than the level of expression of the same protein marker(s) in the normal cell sample of the same tissue type.

Furthermore, cell samples can be isolated from human tumor tissues using means that are known in the art (see, e.g., Vara et al. (2005) *Biomaterials* 26(18):3987-93; Iyer et al. (1998) *J. Biol. Chem.* 273(5):2692-7). For example, the cell sample can be isolated from a human patient with breast cancer. Breast cancer cells can be obtained from other tissues as well, as in the case of metastatic breast cancer. Non-limiting sites of breast cancer-derived metastases can include, but are not limited to, breast, bone, blood, lung, skin, brain, adipose tissue, muscle, gastrointestinal tissues, hepatic tissues, and kidney. Alternatively, cell samples can be obtained commercially from cell line sources as well (e.g., American Type Culture Collections, Mannassas, Va.).

As used herein, the term "breast cell sample" is intended to mean a cell that is isolated from breast tissue. Breast cell samples can be isolated from several non-limiting types of breast tissue including glandular, ductal, stromal, fibrous and lymphatic tissue. In addition, the cell sample can be a metastatic cell isolated from bone, lymphatic tissue, blood, brain, lung, muscle, and skin. Breast or breast cell samples can be isolated from a mammal such as a human, mouse, rat, horse, pig, guinea pig, or chinchilla. The methods of the invention can be used to detect different types of neoplastic cells from breast tissue. Exemplary non-limiting breast cancer cells include lobular neoplasia, ductal carcinoma in situ, infiltrating lobular carcinoma, infiltrating ductal carcinoma, tubular carcinoma, mucinous carcinoma, medullary carcinoma, phylloides tumor, inflammatory breast cancer, Paget's disease of the nipple, ductal carcinoma, and breast adenocarcinoma. Breast cancer cell lines are also available from common sources, such as the ATCC cell biology collections (American Type Culture Collections, Mannassas, Va.).

The present invention allows for the detection of cancer in tissues that are of mixed cellular populations such as a mixture of cancer cells and normal cells. In such cases, cancer cells can represent as little as 40% of the tissue isolated for the present invention to determine that the cell sample is tumorigenic. In certain embodiments, the cell sample can be composed of 50% cancer cells for the present invention to detect tumorigenic potential. Cell samples composed of greater than 50% tumorigenic cells can also be used in the present invention. It should be noted that cell samples can be isolated from tissues that are less than 40% tumorigenic cells as long as the cell sample contains a portion of cells that are at least 40% tumorigenic.

In the present invention, levels of expression of housekeeping proteins are used to normalize the signal obtained between patients. As used herein, the term "housekeeping proteins" refers to any protein that has relatively stable or steady expression at the protein level during the life of a cell. Housekeeping proteins can be protein markers that show little difference in expression between cancer cells and normal cells in a particular tissue type (see, e.g., Pandey et al. (2004) *Bioinformatics* 20(17): 2904-2910). In addition, the housekeeping proteins are used to identify the proper signal level by which to compare the cell sample signals between protein microarray experiments.

Another aspect of the invention provides a method of diagnosing cancer in a cell sample. In this method, expression of a protein marker in the potentially cancerous cell is measured. Expression levels for the protein markers can be determined using techniques known in the art. Useful ways to determine such expression levels include, but not limited to, Western blot, protein microarrays, and Enzyme-Linked Immunosorbent Assays ("ELISA") (see, e.g., U.S. Pat. No. 6,955,896; U.S. Pat. No. 6,087,012; U.S. Pat. No. 3,791,932; U.S. Pat. No. 3,850,752; U.S. Pat. No. 4,034,074). Such examples are not intended to limit the potential means for determining the expression of a protein marker in a cell sample. Expression levels of markers on or by potentially cancerous cell samples and normal control cell samples can be compared using standard statistical techniques known to those of skill in the art (see, e.g., Ma et al., (2002) *Methods Mol. Biol.* 196:139-45).

The cancer cell sample can be isolated from a human patient by a physician and tested for expression of protein markers using a focused microarray. In addition, the cancer cell sample can be isolated from an organism that develops a tumor or cancer cells including, but not limited to, mouse, rat, horse, pig, guinea pig, or chinchilla. Cell samples can be stored for extended periods prior to testing or tested immediately upon isolation of the cell sample from the subject. Cell samples can be isolated by non-limiting methods such as surgical excision, aspiration from soft tissues such as adipose tissue or lymphatic tissue, biopsy, or removed from the blood. These methods are known to those of skill in the art.

1.2. Protein-Targeting Agents

Protein marker expression is used to identify tumorigenic potential. Protein markers can be obtained by isolation from a cell sample using any techniques available to one of ordinary skill in the art (see, e.g., Ausubel et. al., *Current Protocols in Molecular Biology*, Wiley and Sons, New York, N.Y., 1999). Isolation of protein markers from the potentially tumorigenic cell sample allows for the generation of target molecules, providing a means for determining the expression level of the protein markers in the potentially tumorigenic cell sample as described below. The protein markers can be isolated from a tissue sample isolated from a human patient. The markers can be isolated from a cytoplasmic fraction or a membrane fraction of the sample. Protein isolation techniques known in the art include, but are not limited to, column chromatography, spin column chromatography, and protein precipitation. Protein markers can be isolated using methods that are taught in, for example, Ausubel et al., *Current Protocols in Molecular Biology*, Vol. 1, John Wiley & Sons, Inc., (1993).

In particular embodiments, the invention provides protein-targeting agents that are comprise antibodies or antigen-binding fragments thereof. These embodiments are described in detail below. Other potential protein targeting agents include, but are not limited to, peptidomimetic compounds, peptides directed to the active sites of an enzyme, nucleic acids, nucleic acid aptamers.

In addition, inhibitors can be used as protein targeting agents to bind to protein markers. Useful inhibitors are compounds that bind to a target protein, and normally reduce the "effective activity" of the target protein in the cell or cell sample. Inhibitors include, but are not limited to, antibodies, antibody fragments such as "Fv," "F(ab')2," "F(ab)," "Dab" and single chains representing the reactive portion of an antibody ("SC-Mab"), peptides, peptidomimetic compounds, and small molecules (see, e.g., Lopez-Alemany et al. (2003) *Am. J. Hematol.* 72(4): 234-42; Miles et al. (1991) *Biochem.* 30(6): 1682-91). Inhibitors can perform their functions through a variety of means including, but not limited to, non-competitive, uncompetitive, and competitive mechanisms. For instance, the triosephosphate isomerase 1, inhibitor N-hydroxy-4-phosphono-butanamide, has been described previously (see, e.g., Verlinde et al. (1989) *Protein Sci.* 1(12): 1578-84).

Protein targeting agents, including antibodies, can be conjugated to non-limiting materials such as magnetic compounds, paramagnetic compounds, proteins, nucleic acids, antibody fragments, or combinations thereof. Furthermore, antibodies can be disposed on an NPV membrane and placed into a dipstick. Antibodies can also be immobilized on a solid support at pre-determined positions such as in the case of a microarray.

Protein targeting agents can be detectably labeled. As used herein, "detectably labeled" means that a targeting agent is operably linked to a moiety that is detectable. By "operably linked" is meant that the moiety is attached to the protein-targeting agent by either a covalent or non-covalent (e.g., ionic) bond. Methods for creating covalent bonds are known (see, e.g., Wong, S. S., *Chemistry of Protein Conjugation and Cross-Linking*, CRC Press 1991; Burkhart et al., *The Chemistry and Application of Amino Crosslinking Agents or Aminoplasts*, John Wiley & Sons Inc., New York City, N.Y., 1999).

According to the invention, a "detectable label" is a moiety that can be sensed. Such labels can be, without limitation, fluorophores (e.g., fluorescein (FITC), phycoerythrin, rhodamine), chemical dyes, or compounds that are radioactive, chemoluminescent, magnetic, paramagnetic, promagnetic, or enzymes that yield a product that may be colored, chemoluminescent, or magnetic. The signal is detectable by any suitable means, including spectroscopic, photochemical, biochemical, immunochemical, electrical, optical or chemical means. In certain cases, the signal is detectable by two or more means. In certain embodiments, protein targeting agents include fluorescent dyes, radiolabels, and chemiluminescent labels, which are examples that are not intended to limit the scope of the invention (see, e.g., Gruber et al. (2000) *Bioconjug. Chem.* 11(5): 696-704).

For example, protein-targeting agents may be conjugated to Cy5/Cy3 fluorescent dyes. These dyes are frequently used in the art (see, e.g., Gruber et al. (2000) *Bioconjug. Chem.* 11(5): 696-704). The fluorescent labels can be selected from a variety of structural classes, including the non-limiting examples such as 1- and 2-aminonaphthalene, p,p'diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a, 4a-diaza-s-indacene dyes and fluorescent proteins (e.g., green fluorescent protein, phycobiliprotein).

1.3. Antibodies for Detection of Protein Markers

Aspects of the present invention utilize monoclonal and polyclonal antibodies as protein-targeting agents directed specifically against certain protein markers. Useful protein markers include, but are not limited to, cytokeratin 19, cathepsin D, ezrin, A-CRABP II, slc9a3rl, and HER-2. Anti-protein marker antibodies, both monoclonal and polyclonal, for use in the invention are available from several commercial sources (e.g., Santa Cruz Biotechnology, Santa Cruz, Calif.; and Biogenesis, Inc., Kingston, N.H.). Cytokeratin 19, cathepsin D, ezrin, A-CRABP II, slc9a3rl, and HER-2 antibodies can be administered to a patient orally, subcutaneously, intramuscularly, intravenously, or interperitoneally.

As used herein, the term "polyclonal antibodies" means a population of antibodies that can bind to multiple epitopes on an antigenic molecule. A polyclonal antibody is specific to a particular epitope on an antigen, while the entire pool of polyclonal antibodies can recognize different epitopes. In addition, polyclonal antibodies developed against the same antigen can recognize the same epitope on an antigen, but with varying degrees of specificity. Polyclonal antibodies can be isolated from multiple organisms including, but not limited to, rabbit, goat, horse, mouse, rat, and primates. Polyclonal antibodies can also be purified from crude serums using techniques known in the art (see, e.g., Ausubel, et al., Current Protocols in Molecular Biology, Vol. 1, pp. 4.2.1-4.2.9, John Wiley & Sons, Inc., 1996).

The term "monoclonal antibody", as used herein, refers to an antibody obtained from a population of substantially homogenous antibodies, i.e., the individual antibodies comprising the population are identical except for possible naturally occurring mutations that may be present in minor amounts. Monoclonal antibodies are highly specific, being directed against a single antigenic site. By their nature, monoclonal antibody preparations are directed to a single specific determinant on the target. Novel monoclonal antibodies or fragments thereof mean in principle all immunoglobulin classes such as IgM, IgG, IgD, IgE, IgA, or their subclasses or mixtures thereof. Non-limiting examples of subclasses include the IgG subclasses IgG1, IgG2, IgG3, IgG2a, IgG2b, IgG3, or IgGM. The IgG subtypes IgG1/κ and IgG2b/κ are also included within the scope of the present invention. Antibodies can be obtained commercially from, e.g., BioMol International LP (Plymouth Meeting, Pa.), BD Biosciences Pharmingen (San Diego, Calif.), and Cell Sciences, Inc. (Canton, Mass.).

The monoclonal antibodies herein include hybrid and recombinant antibodies produced by splicing a variable (including hypervariable) domain of an anti-protein marker antibody with a constant domain (e.g., "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab)$_2$, and Fv), so long as they exhibit the desired biological activity. (see, e.g., U.S. Pat. No. 4,816,567; Mage and Lamoyi, in *Monoclonal Antibody Production Techniques and Applications*, (Marcel Dekker, Inc., New York 1987, pp. 79-97). Thus, the modified "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method (see, e.g., Kohler and Milstein (1975) *Nature* 256:495) or can be made by recombinant DNA methods (U.S. Pat. No. 4,816,567). The monoclonal antibodies can also be isolated from phage libraries generated using the techniques described in the art (see, e.g., McCafferty et al. (1990) *Nature* 348:552-554).

Alternative methods for producing antibodies can be used to obtain high affinity antibodies. Antibodies can be obtained from human sources such as serum. Additionally, monoclonal antibodies can be obtained from mouse-human heteromyeloma cell lines by techniques known in the art (see, e.g., Kozbor (1984) *J. Immunol.* 133, 3001; Boerner et al., (1991) *J. Immunol.* 147:86-95). Methods for the generation of human monoclonal antibodies using phage display, transgenic mouse technologies, and in vitro display technologies are known in the art and have been described previously (see, e.g., Osbourn et al. (2003) *Drug Discov. Today* 8: 845-51; Maynard and Georgiou (2000) Ann. Rev. Biomed. Eng. 2: 339-76; U.S. Pat. Nos. 4,833,077; 5,811,524; 5,958,765; 6,413,771; and 6,537,809).

Aspects of the invention also utilize polyclonal and monoclonal antibodies for the detection of cytokeratin 19, cathepsin D, ezrin, A-CRABP II, slc9a3rl, and HER-2.

1.4. Detection of Protein Markers from Biological Fluids

An aspect of the present invention includes an assay for the detection of any protein marker using a protein-targeting agent to bind to the protein marker. The protein marker is typically a peptide, polypeptide, protein, glycoprotein, or proteolipid. The protein-targeting agent comprises antigens and antibodies thereto; haptens and antibodies thereto; and hormones, ligands, vitamins, metabolites and pharmacological agents, and their receptors and binding substances. The protein-targeting agent may be an immunologically-active polypeptide or protein or molecular weight between 1,000 Daltons and 10,000,000 Daltons, such as an antibody or antigenic polypeptide or protein, or a hapten of molecular weight between 100 Daltons and 1,500 Daltons. Protein-targeting agents can bind to protein markers that are obtained from biological fluids. As used herein, the term "biological fluids" means aqueous or semi-aqueous liquids isolated from an organism in which biological macromolecules may be identified or isolated. Biological fluids may be disposed internally as in the case of blood, bile, serum, or cerebrospinal fluid. Biological fluids can be excreted as in the non-limiting cases of urine, saliva, sweat, tears, mucosal secretions, seminal fluid, sperm, and sebaceous secretions.

For detection of markers in biological fluids, detection devices can be used that are in the form of a "dipstick." Such devices are known in the art, and have been applied to detecting protein markers in serum and other biological fluids (see, e.g., U.S. Pat. No. 4,390,343). In some instances, a dipstick-type device can be comprised of analytical elements where protein-targeting agents, such as antibodies, inhibitors, organic molecules, peptidomimetic compounds, ligands, organic compounds, or combinations thereof, are incorporated into a gel. The gel can be comprised of non-limiting substances such as agarose, gelatin or PVP (see, e.g., U.S. Pat. No. 4,390,343). The gel can be contained within an analytical region for reaction with a protein marker.

The "dipstick" format (see, e.g., U.S. Pat. Nos. 5,275,785, 5,504,013, 5,602,040, 5,622,871 and 5,656,503) typically consists of a strip of porous material having a biological fluid sample-receiving end, a reagent zone and a reaction zone. As used herein, the term "reagent zone" means the area within the dipstick in which the protein-targeting agent and the protein markers in the biological sample come into contact. By the term "reaction zone", is meant the area within the dipstick in which an immobilized binding agent captures the protein-targeting agent/protein marker complex. As used herein, the term "binding agent" refers to any molecule or group of molecules that can bind, interact, or associate with a protein-targeting agent/protein marker complex.

In certain embodiments, the biological fluid sample is wicked along the assay device starting at the sample-receiving end and moving into the reagent zone. The protein marker(s) to be detected binds to a protein-targeting agent incorporated into the reagent zone, such as a labeled protein-targeting agent, to form a complex. For example, a labeled antibody can be the protein-targeting agent, which complexes specifically with the protein marker. In other examples, the protein-targeting agent can be a receptor that binds to a protein marker in a receptor:ligand complex. In other examples, an inhibitor is used to bind to a protein marker, thereby forming a complex with the protein marker targeted by the particular inhibitor. In some examples, peptidomimetic compounds are used to bind to protein markers to mimic the interaction of a protein marker with a normal peptide. In yet other examples, the protein-targeting agent can be an organic molecule capable of associating with the protein marker. In all cases, the protein-targeting agent has a label. The labeled protein-targeting agent-protein marker complex then migrates into the reaction zone, where the complex is captured by another specific binding partner firmly immobilized in the reaction zone. Retention of the labeled complex within the reaction zone thus results in a visible readout.

A number of different types of other useful assays that measure the presence of a protein marker are well known in the art. Immunoassays may be homogeneous, i.e. performed in a single phase, or heterogeneous, where antigen or antibody is linked to an insoluble solid support upon which the assay is performed. Sandwich or competitive assays may be performed. The reaction steps may be performed simultaneously or sequentially. Threshold assays may be performed, where a predetermined amount of analyte is removed from the sample using a capture reagent before the assay is performed, and only analyte levels of above the specified concentration are detected. Assay formats include, but are not limited to, for example, assays performed in test tubes, wells or on immunochromatographic test strips, as well as dipstick, lateral flow or migratory format immunoassays.

In certain embodiments, a lateral flow test immunoassay device is used. In such devices, a membrane system forms a single fluid flow pathway along the test strip. The membrane system includes components that act as a solid support for immunoreactions. For example, porous or bibulous or absorbent materials can be placed on a strip such that they partially overlap, or a single material can be used, in order to conduct liquid along the strip. The membrane materials can be supported on a backing, such as a plastic backing. The test strip includes a glass fiber pad, a nitrocellulose strip and an absorbent cellulose paper strip supported on a plastic backing.

Antibodies that specifically bind with the target protein marker are immobilized on the solid support. The antibodies can be bound to the test strip by adsorption, ionic binding, van der Waals adsorption, electrostatic binding, or by covalent binding, by using a coupling agent, such as glutaraldehyde. For example, the antibodies can be applied to the conjugate pad and nitrocellulose strip using standard dispensing methods, such as a syringe pump, airbrush, ceramic piston pump or drop-on-demand dispenser. A volumetric ceramic piston pump dispenser can be used to stripe antibodies that bind the analyte of interest, including a labeled antibody conjugate, onto a glass fiber conjugate pad and a nitrocellulose strip.

The test strip can be treated, for example, with sugar to facilitate mobility along the test strip or with water-soluble non-immune animal proteins, such as albumins, including bovine (BSA), other animal proteins, water-soluble polyamino acids, or casein to block non-specific binding sites.

1.5. Cancer Diagnosis and Prediction Analysis

Cancer diagnoses can be performed by comparing the levels of expression of a protein marker or a set of protein markers in a potentially neoplastic cell sample to the levels of expression for a protein marker or a set of protein markers in a normal control cell sample of the same tissue type. Alternatively, the level of expression of a protein marker or a set of protein markers in a potentially cancerous cell sample is compared to a reference pool of protein markers that represents the level of expression for a protein marker or a set of protein markers in a normal control population (herein termed "training set"). The training set also includes the data for a population that has a known tumor or class of tumors. This data represents the average level of expression that has been determined for the neoplastic cells isolated from the tumor or class of tumors. It also has data related to the average level of expression for a protein marker or set of protein markers for normal cells of the same cell type within a population. In these embodiments, the algorithm compares newly generated expression data for a particular protein marker or set of protein markers from a cell sample isolated from a patient containing potentially neoplastic cells to the levels of expression for the same protein marker or set of protein markers in the training set. The algorithm determines whether a cell sample is neoplastic or normal by aligning the level of expression for a protein marker or set of protein markers with the appropriate group in the training set. In certain embodiments, software for performing the statistical manipulations described herein can be provided on a computer connected by data link to a data generating device, such as a microarray reader.

Statistical analysis of the levels of expression of protein markers in a cell sample to determine cancer state does not require a particular algorithm or set of particular algorithms. Any algorithm can be used in the present invention so long as it can discriminate between statistically significant and statistically insignificant differences in the levels of expression of protein markers in a cell sample as compared to the levels of expression of the same protein markers in a normal cell sample of the same tissue type.

Class prediction algorithms can be utilized to differentiate between the levels of expression of markers in a cell sample and the levels of expression of markers in a normal cell sample (Vapnik, *The Nature of Statistical Learning Theory*, Springer Publishing, 1995). Exemplary, non-limiting algorithms include, but are not limited to, compound covariate predictor, diagonal linear discriminant analysis, nearest neighbor predictor, nearest centroid predictor, and support vector machine predictor (Simon et al., *Design and Analysis of DNA Microarray Investigations: An Artificial Intelligence Milestone*, Springer Publishing, 2003). These statistical tests are well known in the art, and can be applied to ELISA or data generated using other protein expression determination techniques such as dot blotting, Western Blotting, and protein microarrays (see, e.g., U.S. Patent Application No. 2005/0239079).

In some embodiments, an increased level of expression in the potentially cancerous cell sample indicates that cancer cells exist in the cell sample. In such cancerous cell samples, protein markers showing increased levels of expression include, but are not limited to cytokeratin 19, cathepsin D, ezrin, A-CRABP II, slc9a3rl, and HER-2. The algorithm makes the class prediction based upon the overall levels of expression found in the cell sample as compared to the levels of expression in the training set. It should be noted that, in some instances, one protein marker can be used to classify a gene as either neoplastic or normal. Two or more protein markers can also be used to properly classify a cell sample as neoplastic or normal. In particular, three protein markers can be used for classification purposes. Four protein markers can be used to identify neoplastic cells within a cell sample. Five protein markers can be used to identify neoplastic cells in a cell sample. Furthermore, six or more protein markers can be used to properly classify cell samples into either the neoplastic cell class or the non-neoplastic cell class.

The type of analysis detailed above compares the level of expression for the protein marker(s) in the cell sample to a training set containing reference pools of protein that are representative of a normal population and a neoplastic population. In certain embodiments, the training set can be obtained with kits that can be used to determine the level of expression of protein marker(s) in a patient cell sample. Alternatively, an investigator can generate new training sets using protein expression reference pools that can be obtained from commercial sources such as Asterand, Inc. (Detroit, Mich.). Comparisons between the training sets and the cell samples are performed using standard statistical techniques that are well known in the art, and include, but are not limited to, the ArrayStat 1.0 program (Imaging Research, Inc.). Statistically significant increased levels of expression in the cell sample of protein marker(s) indicate that the cell sample contains a cancer cell or cells with tumorigenic potential. Also, standard statistical techniques such as the Student T test are well known in the art, and can be used to determine statistically significant differences in the levels of expression for protein markers in a patient cell sample (see, e.g., Piedra et al. (1996) *Ped. Infect. Dis. J.* 15:1). In particular, the Student T test is used to identify statistically significant changes in expression using protein microarray analysis or ELISA analysis (see, e.g., Piedra et al. (1996) *Ped. Infect. Dis. J.* 15:1).

1.6 Focused Microarray

The invention allows for protein-targeting agents to be immobilized on a solid support. In certain embodiments, the support can be a bead or flat surface similar to a slide. Such a microarray can determine the protein expression of certain markers in a chemotherapeutic drug-resistant cancer cell sample and the protein expression of a multi-drug-sensitive control cell of the same tissue type. The microarray can also be used to determine the presence of a non-MDR neoplastic cell in a cell sample. Protein microarrays can be prepared by methods disclosed in, e.g., U.S. Pat. Nos. 6,087,102, 6,139,831, and 6,087,103.

Protein-targeting agents conjugated to the surface of the protein microarray can be bound by detectably labeled protein markers isolated from a cell sample. This method of detection can be termed "direct labeling" because the protein marker, which is the target, is labeled. In other embodiments, protein markers can be bound by protein-targeting agents, and then subsequently bound by a detectably labeled antibody specific for the protein marker. These methods are termed "indirect labeling" because the detectable label is associated with a secondary antibody or other protein-targeting agent. An overview of protein microarray technology in general can be found in Mitchell, (2002) *Nature Biotech.* 20: 225-229, the contents of which are incorporated herein by reference.

1.7 Kits

Aspects of the invention additionally provide kits for detecting neoplasms, such as breast cancer, in a cell sample. The kits include targeting agents for the detection of cytokeratin 19, cathepsin D, ezrin, A-CRABP II, slc9a3rl, and HER-2. The kits also can include targeting agents for the detection of vimentin, HSC70, and nucleophosmin. A patient that potentially has a tumor or the potential to develop a tumor ("in need thereof") can be tested for the presence of a tumor or tumor potential by determining the level of expression of targeting agents in a cell sample derived from the patient.

The kit comprises labeled binding agents capable of detecting cytokeratin 19, cathepsin D, ezrin, A-CRABP II, slc9a3rl, and HER-2 in a biological sample, as well as means for determining the amount of these protein markers in the sample, and means for comparing the amount of the protein markers in the potentially cancerous sample with a standard (e.g., normal non-neoplastic cells). The binding agents can be packaged in a suitable container. The kit can further comprise instructions for using the binding agents to detect the protein markers, as well as other neoplasm-associated markers. Such a kit can comprise, e.g., one or more antibodies, or fragments thereof as binding agents that bind specifically to at least a portion of a protein marker.

The kit can also contain a second probe for detection of housekeeping protein expression. These probes advantageously allow health care professionals to obtain an additional data point to determine whether chemotherapeutic drug resistance exists. The probes can be any binding agents such as labeled antibodies, or fragments thereof specific for the housekeeping genes. Alternatively or additionally, the probes can be inhibitors, peptidomimetic compounds, peptides, and/or small molecules.

Data related to the levels of expression of the selected protein markers in normal tissues and neoplasms can be supplied in a kit or individually in the form of a pamphlet, document, floppy disk, or computer CD. The data can represent patient pools developed for a particular population (e.g., Caucasian, Asian, etc.) and is tailored to a particular cancer type. Such data can be distributed to clinicians for testing patients for the presence of a neoplasm such as breast cancer. A clinician obtains the levels of expression for a protein marker or set of protein markers in a particular patient. The clinician then compares the expression information obtained from the patient to the levels of expression for the same protein marker or set of protein markers that had been determined previously for both normal control and cancer patient pools. A finding that the level of expression for the protein marker or the set of protein markers is similar to the normal patient pool data indicates that the cell sample obtained from the patient is not neoplastic. A finding that the level of expression for the protein marker or the set of protein markers is similar to the cancer patient pool data indicates that the cell sample obtained from the patient is neoplastic.

1.8 Testing

The diagnostic methods, according to the invention, were tested for their ability to diagnose cancer in cell samples isolated from human subjects suffering from breast cancers.

Sample materials were obtained from Asterand, Inc. (Detroit, Mich.), Cytomix LLC (Lexington, Mass.), and Biochain Institute, Inc. (Hayward, Calif.). Standard clinical and pathological reports were available for each cancer patient included in this study. For the breast panel, 71 tumors and 27 normal tissues were used.

The expression levels of 6 proteins of interest were analyzed for differential expression in breast samples from 71 tumor patients and 27 healthy controls by Western blotting and ELISA assays. The proteins were cytokeratin 19, ezrin, cathepsin D, A-CRABP II, slc9a3rl, and HER-2. As shown in FIGS. 1-6, these proteins showed differential expression between normal and neoplastic breast tissues. Therefore, these proteins were biomarkers for breast cancer.

Figure 1B:
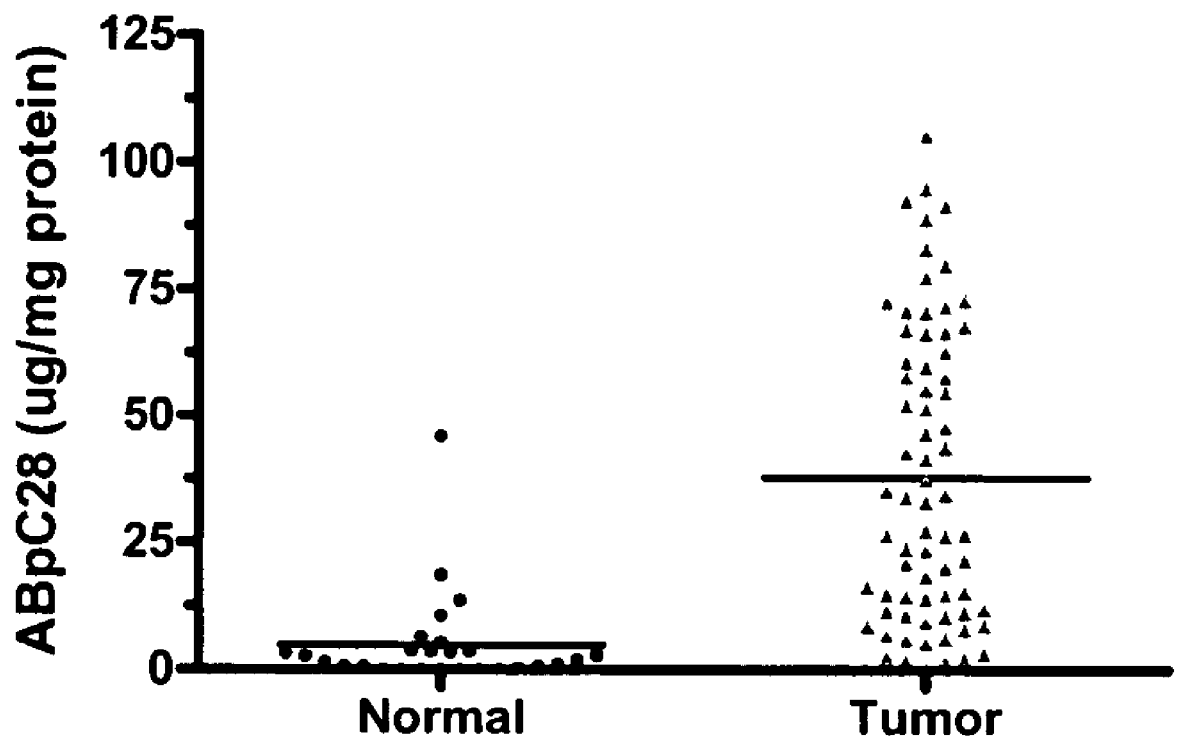
FIG. 1B is a graphic representation showing the results of an ELISA analysis comparing the levels of expression of cytokeratin 19 in normal breast tissue subjects and breast cancer patients.

Cytokeratin 19 was found to be up-regulated in breast tumors when compared to normal tissues (FIG. 1A). Western blot analysis showed that in most cases, protein expression was up-regulated. To confirm these results, ELISA analysis was performed (FIG. 1B). Quantification of cytokeratin 19 expression by ELISA showed that its expression levels were increased by 7.9-fold in tumors as compared to normal tissues. Therefore, cytokeratin 19 was shown to be a reliable predictor of breast neoplasms in human subjects.

Figure 2A:
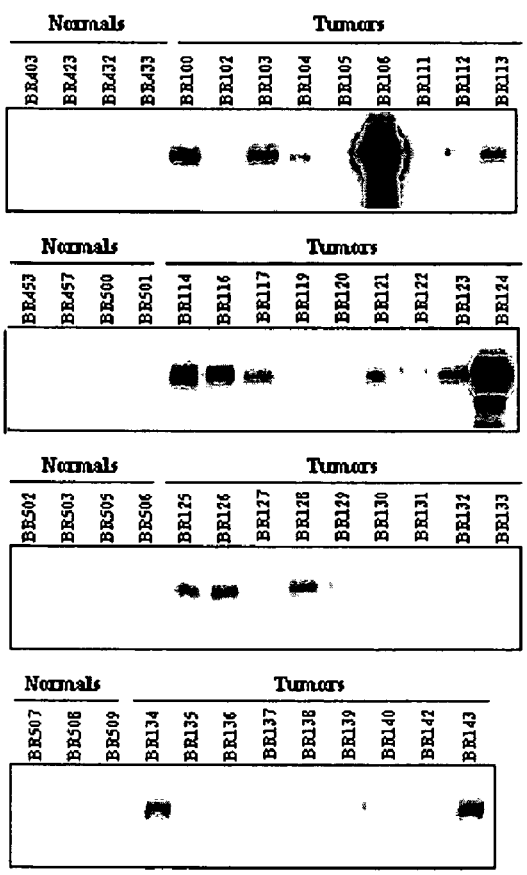
FIG. 2A is a photographic representation of 8 different immunoblots probed with anti-HER-2 antibody that shows the level of expression of HER-2 in tissue samples from normal subjects ("Normals") and breast cancer patients ("Tumors"), normal and tumor samples are identified by the BR number provided.
Figure 2A:
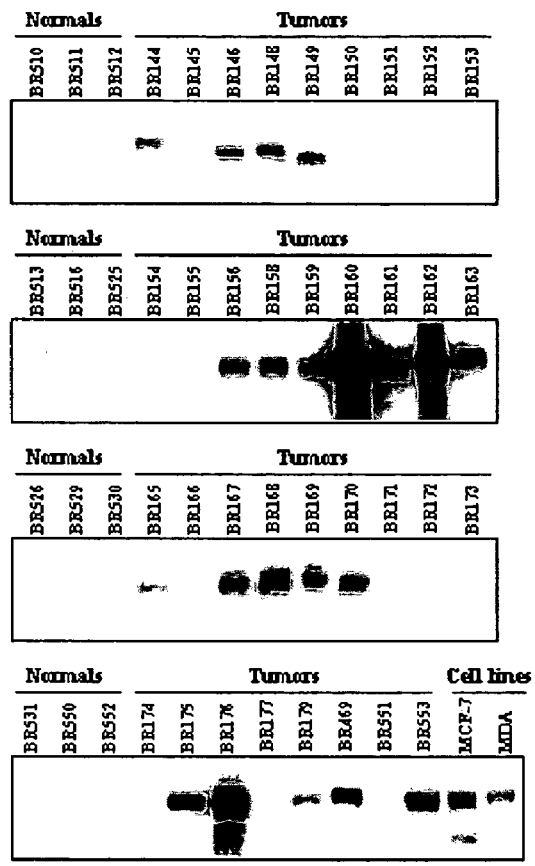
Figure 2B:
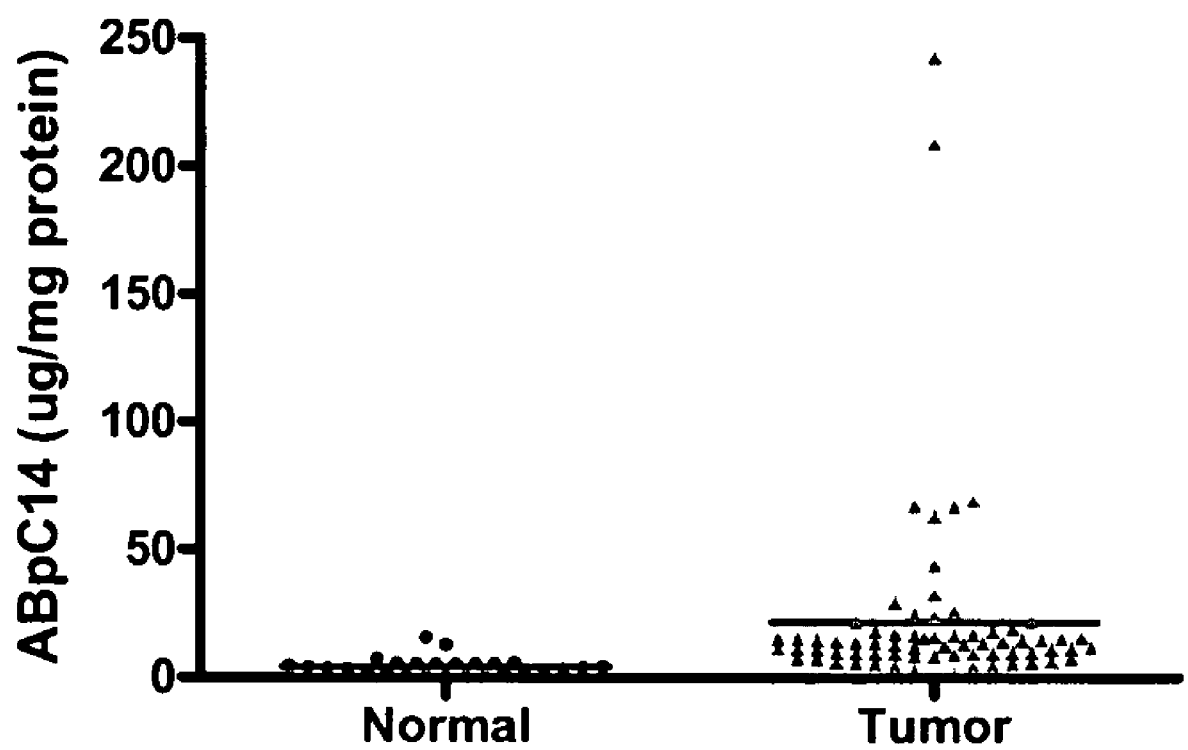
FIG. 2B is a graphic representation showing the results of an ELISA analysis comparing the levels of expression of HER-2 in normal breast tissue subjects and breast cancer patients.
Figure 3A:
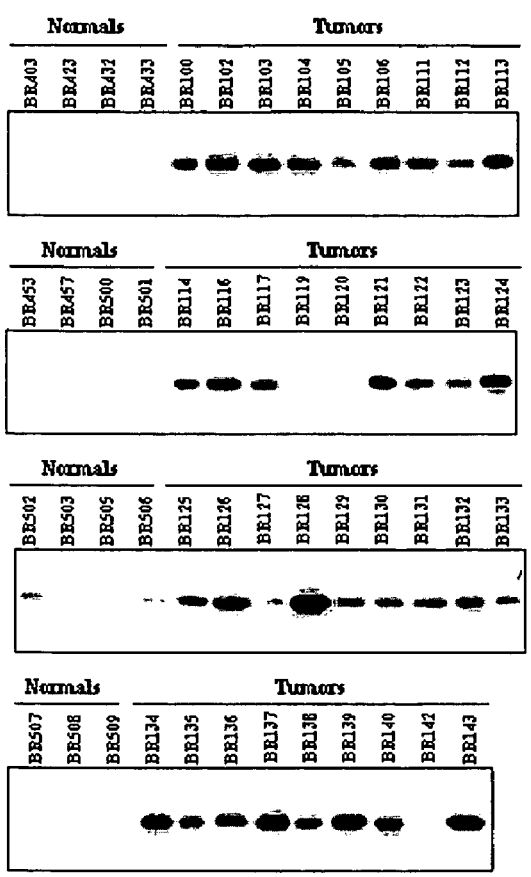
FIG. 3A is a photographic representation of 8 different immunoblots probed with anti-cathepsin D antibody that shows the level of expression of cathepsin δin tissue samples from normal subjects ("Normals") and breast cancer patients ("Tumors"), normal and tumor samples are identified by the BR number provided.
Figure 3A:
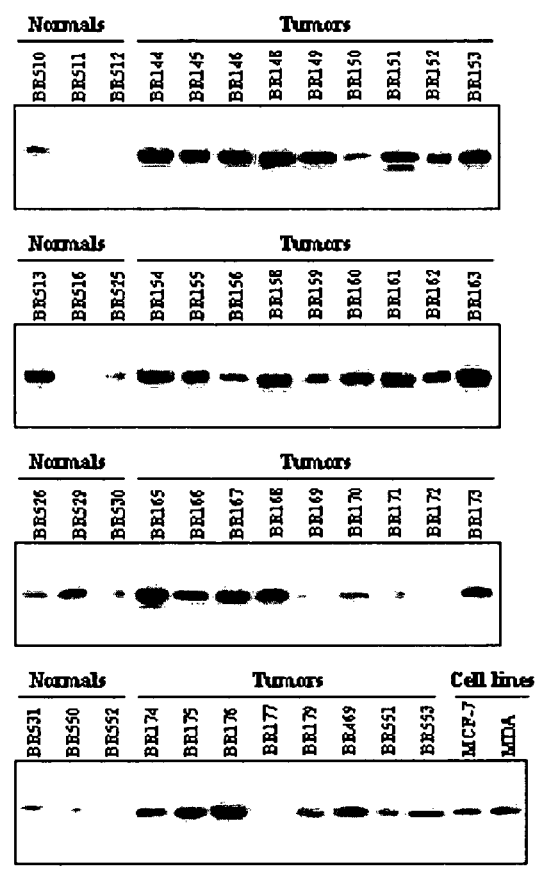
Figure 3B:
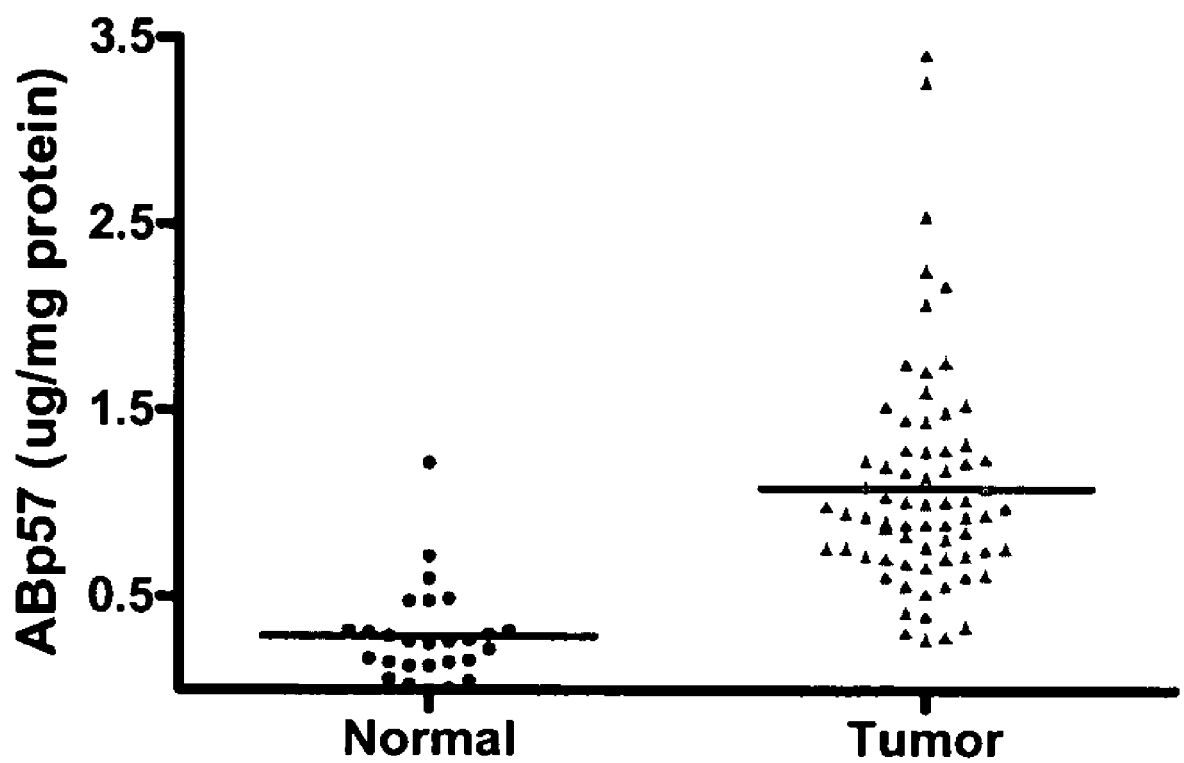
FIG. 3B is a graphic representation showing the results of an ELISA analysis comparing the levels of expression of cathepsin D in normal breast tissue subjects and breast cancer patients.

In addition, HER-2 showed a 5.2-fold increase in tumors as compared to normal tissues (FIG. 2A). These results were confirmed by ELISA, which showed that the majority of neoplastic tissues had increased expression of HER-2 marker in the cell samples (FIG. 2B). In addition to HER-2, cathepsin D showed increased levels of expression in neoplastic tissues as compared to normal subject tissues (FIG. 3A). Western blot analysis established that few normal subjects showed increased levels of expression of HER-2. These results were confirmed by ELISA techniques, which showed that most breast cancer patients had higher levels of HER-2 expression than their normal counterparts (FIG. 3B).

Figure 4A:
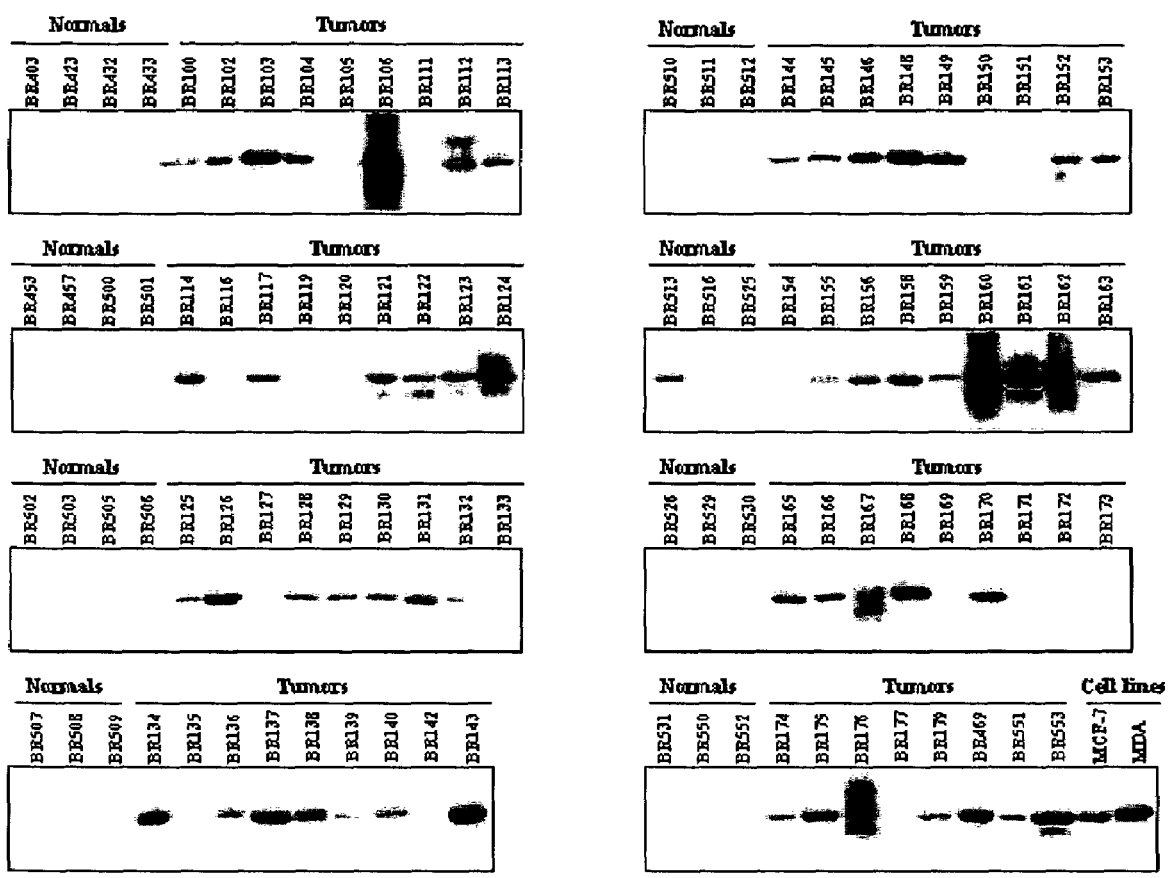
FIG. 4A is a photographic representation of 8 different immunoblots probed with anti-ezrin antibody that shows the level of expression of ezrin in tissue samples from normal subjects ("Normals") and breast cancer patients ("Tumors"), normal and tumor samples are identified by the BR number provided.
Figure 4B:
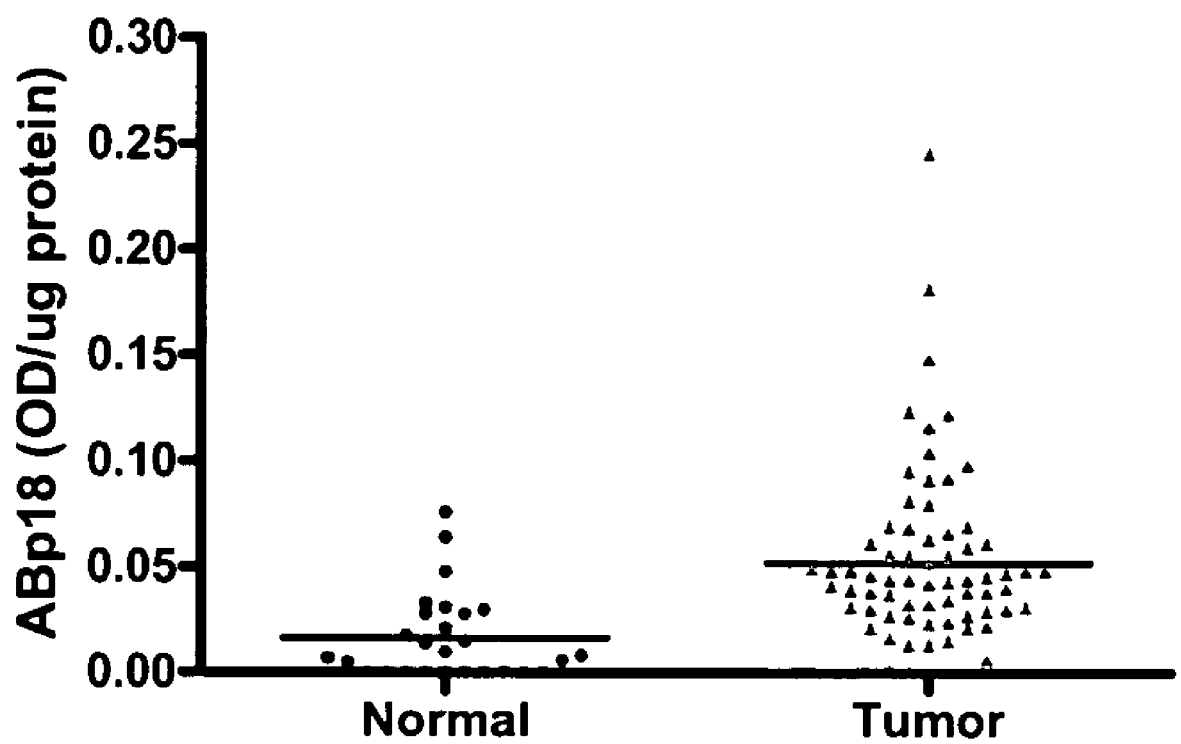
FIG. 4B is a graphic representation showing the results of an ELISA analysis comparing the levels of expression of ezrin in normal breast tissue subjects and breast cancer patients.

Moreover, ezrin protein levels were found to be significantly increased in tumor patient samples as compared to normal subject samples (FIG. 4A). ELISA and Western blot analysis established that most individuals containing tumor tissues had 3.7-fold higher levels of ezrin expression at the protein level than their normal counterparts (FIGS. 4A and 4B).

Figure 5A:
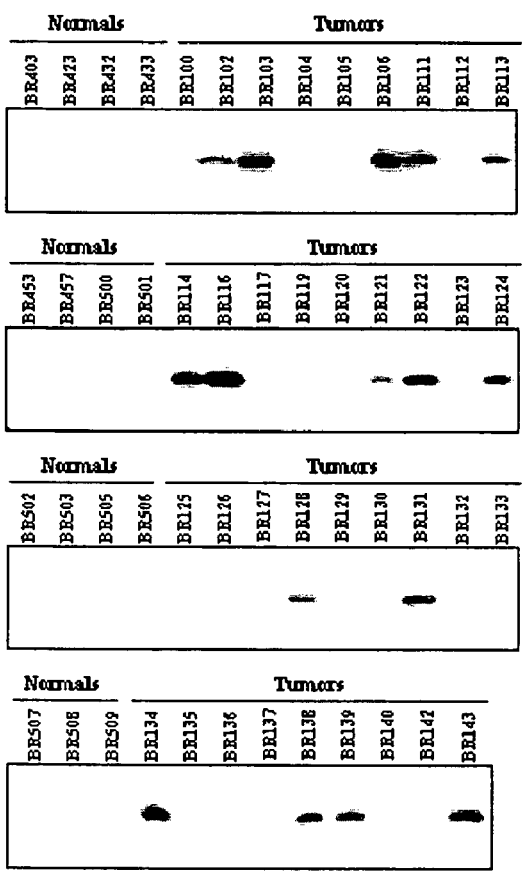
FIG. 5A is a photographic representation of 8 different immunoblots probed with anti-ACRABPII antibody that shows the level of expression of ACRABPII in tissue samples from normal subjects ("Normals") and breast cancer patients ("Tumors"), normal and tumor samples are identified by the BR number provided.
Figure 5A:
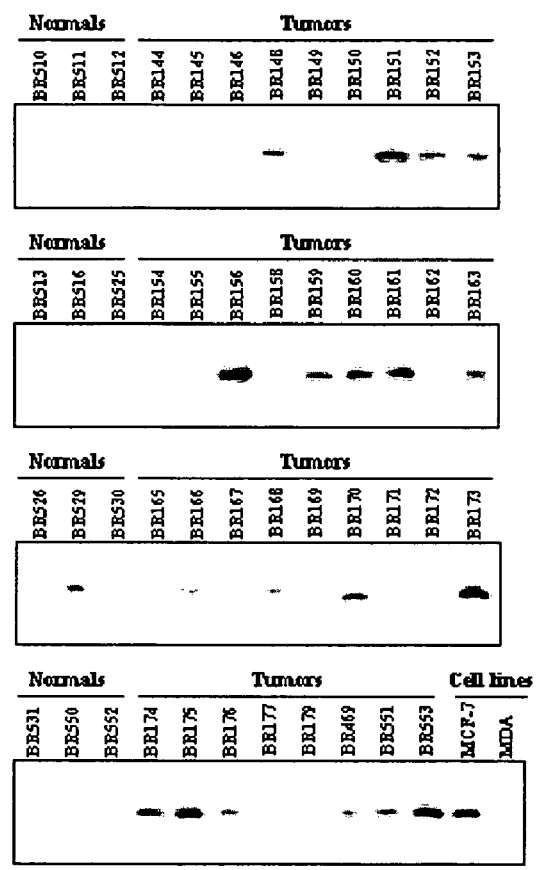
Figure 5B:
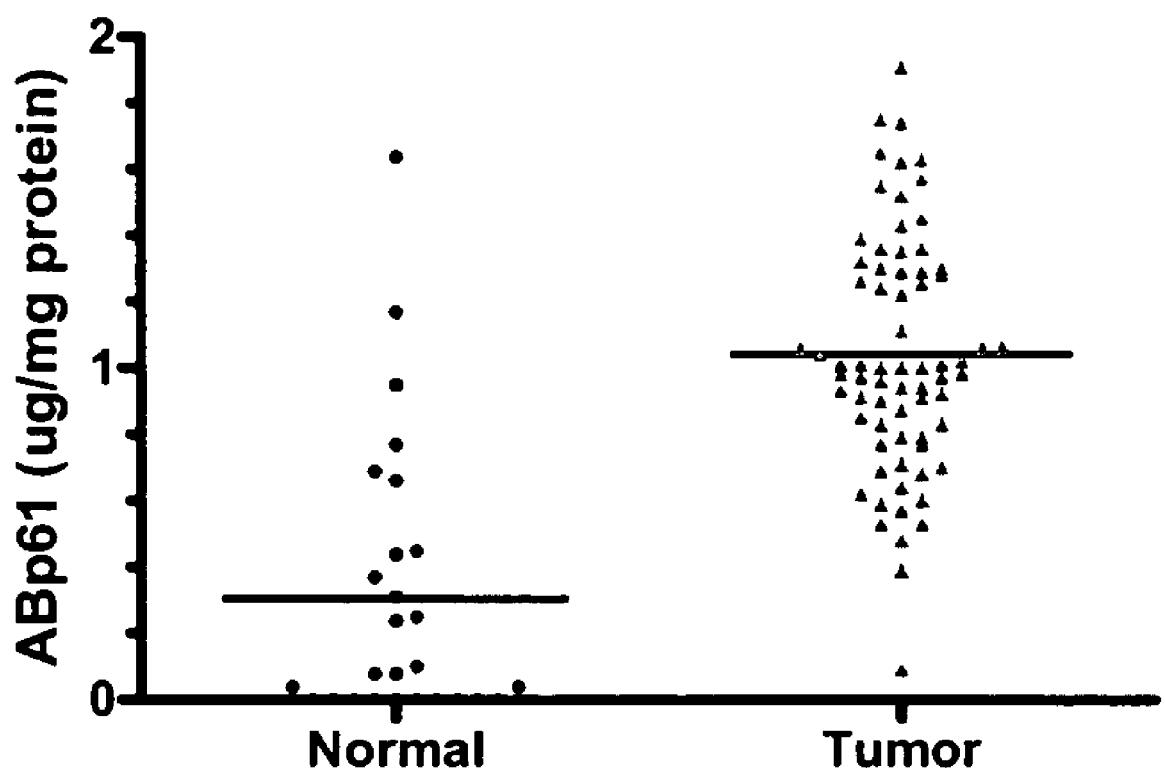
FIG. 5B is a graphic representation showing the results of an ELISA analysis comparing the levels of expression of ACRABPII in normal breast tissue subjects and breast cancer patients.

ACRABPII protein expression levels were also increased in tumor patients as compared to normal subjects (FIGS. 5A and 5B). Breast cancer patients had 3.4-fold higher levels of ACRABPII in tumor tissues than normal subjects. In addition, little overlap was observed between populations with respect to ACRABPII expression when analyzed by ELISA (FIG. 5B).

Figure 6A:
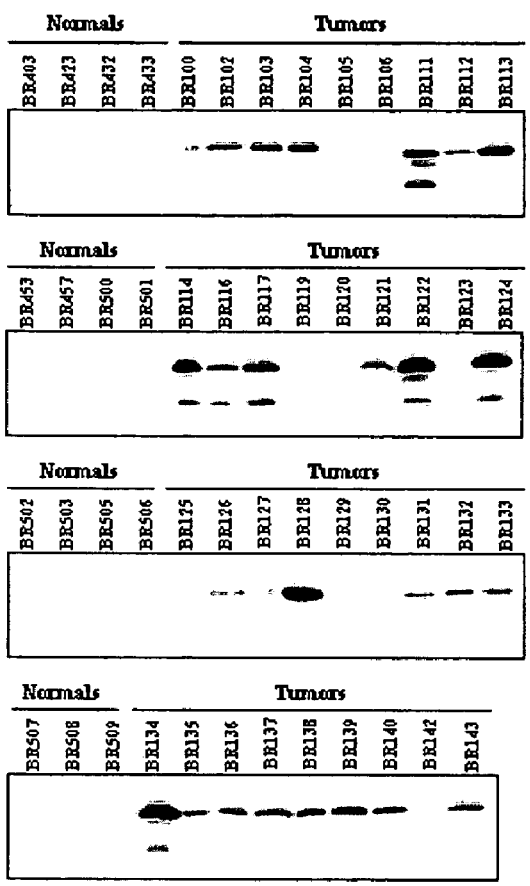
FIG. 6A is a photographic representation of 8 different immunoblots probed with anti-slc9a31 antibody that shows the level of expression of slc9a31 in tissue samples from normal subjects ("Normals") and breast cancer patients ("Tumors"), normal and tumor samples are identified by the BR number provided.
Figure 6A:
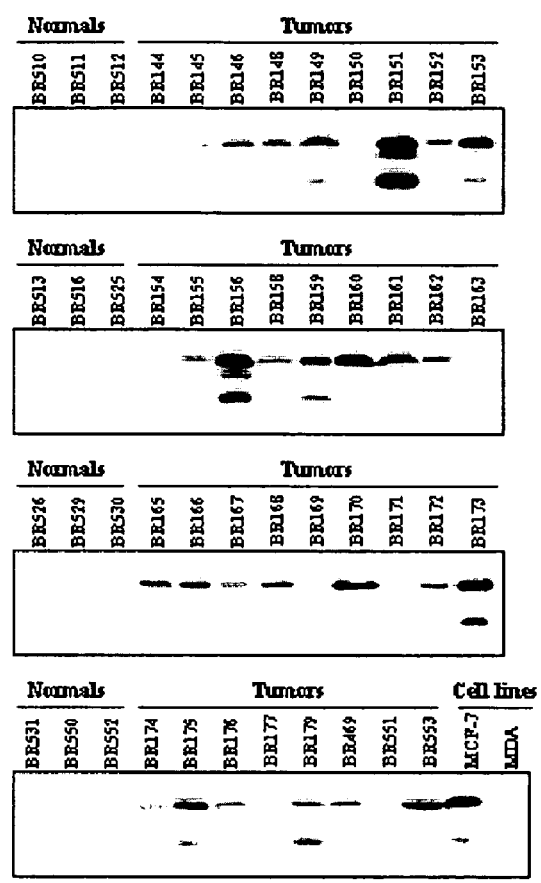
Figure 6B:
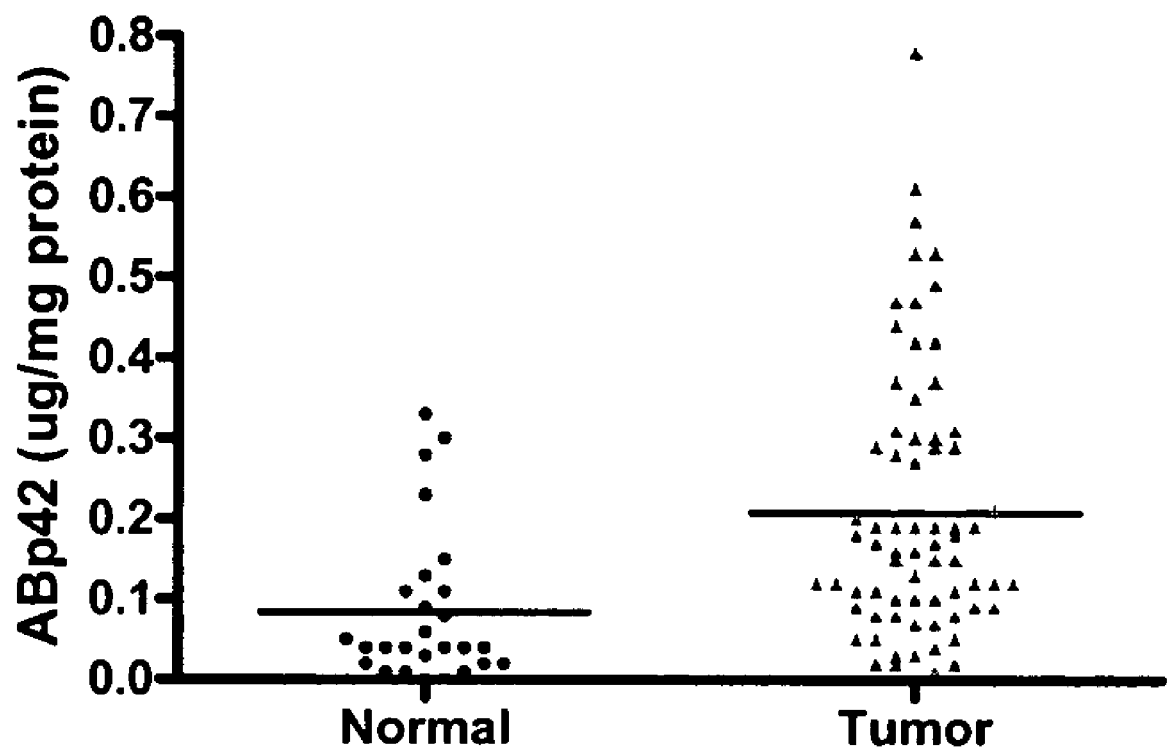
FIG. 6B is a graphic representation showing the results of an ELISA analysis comparing the levels of expression of slc9a31 in normal breast tissue subjects and breast cancer patients.
Figure 7:
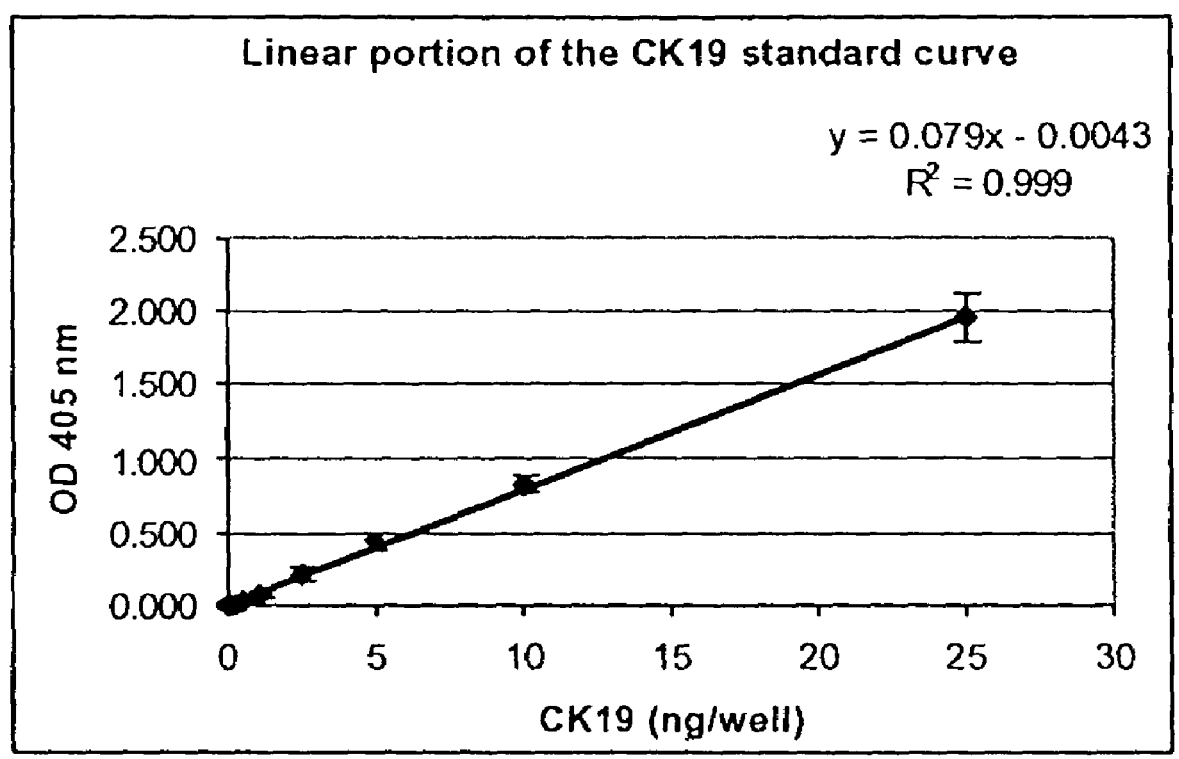
FIG. 7 is a graphic representation of the linear portion of a standard curve produced using recombinant cytokeratin 19 as the target in an ELISA assay using an anti-cytokeratin 19 monoclonal antibody and a secondary anti-mouse IgG antibody conjugated to horseradish peroxidase.
Figure 8:
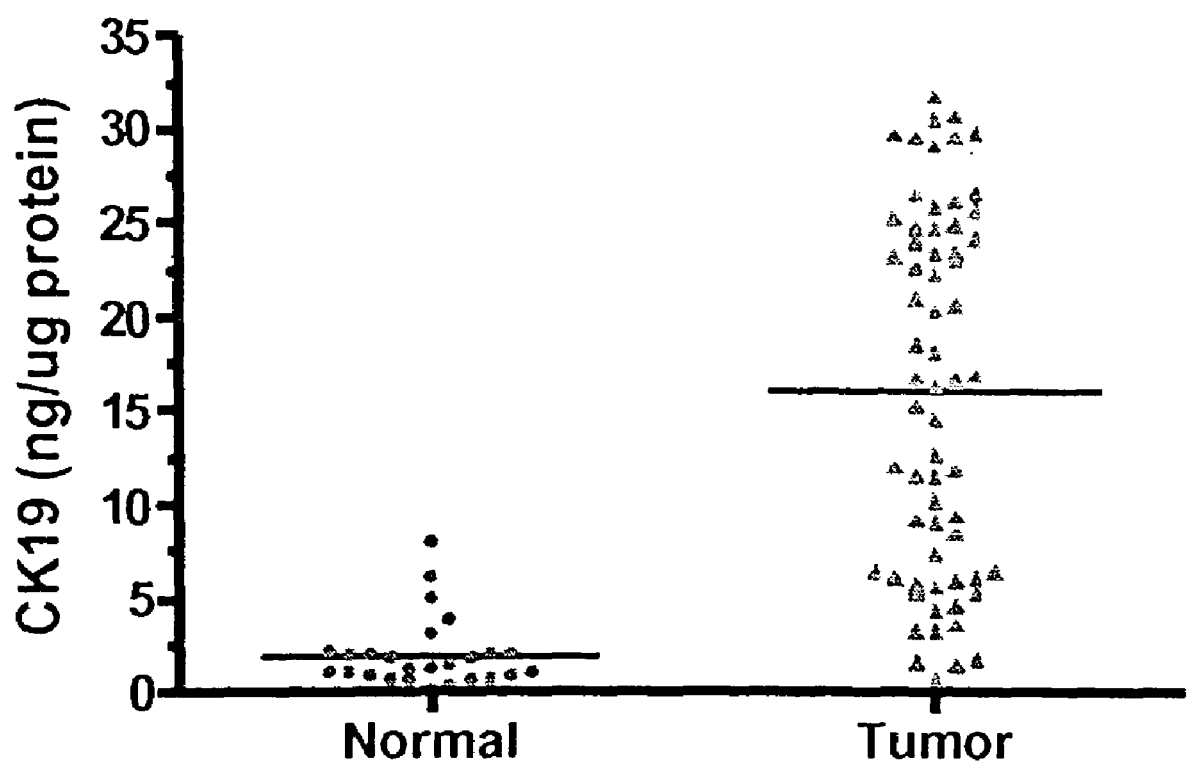
FIG. 8 is a graphic representation showing the results of an ELISA analysis comparing the levels of expression of cytokeratin 19 in normal breast tissue subjects and breast cancer patients.
Figure 9:
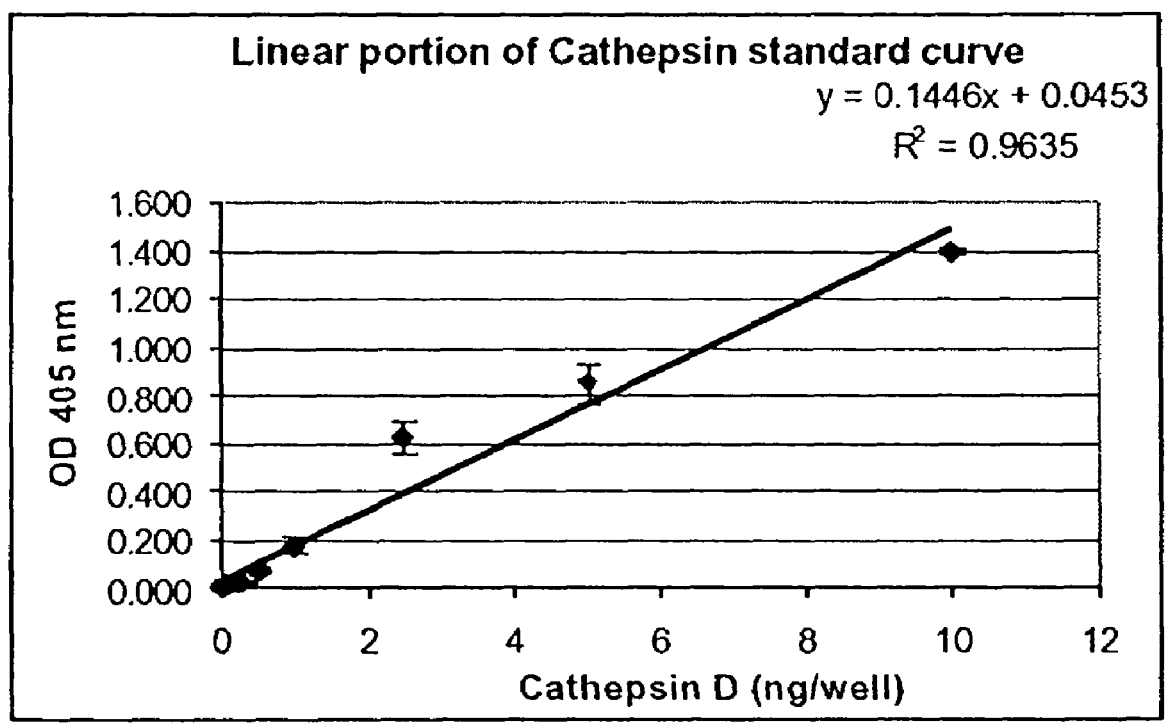
FIG. 9 is a graphic representation of the linear portion of a standard curve produced using recombinant cathepsin D as the target in an ELISA assay using an anti-cathepsin D monoclonal antibody and a secondary anti-mouse IgG antibody conjugated to horseradish peroxidase.
Figure 10:
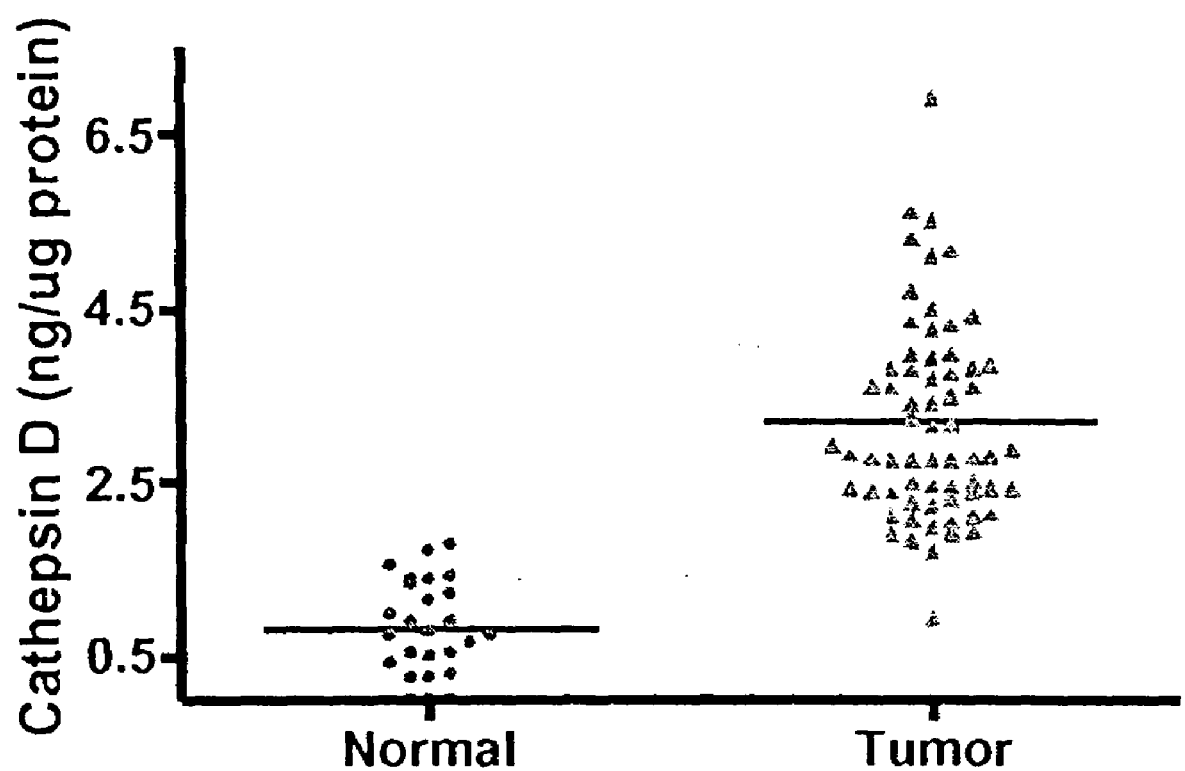
FIG. 10 is a graphic representation showing the results of an ELISA analysis comparing the levels of expression of cathepsin D in normal breast tissue subjects and breast cancer patients.
Figure 11:
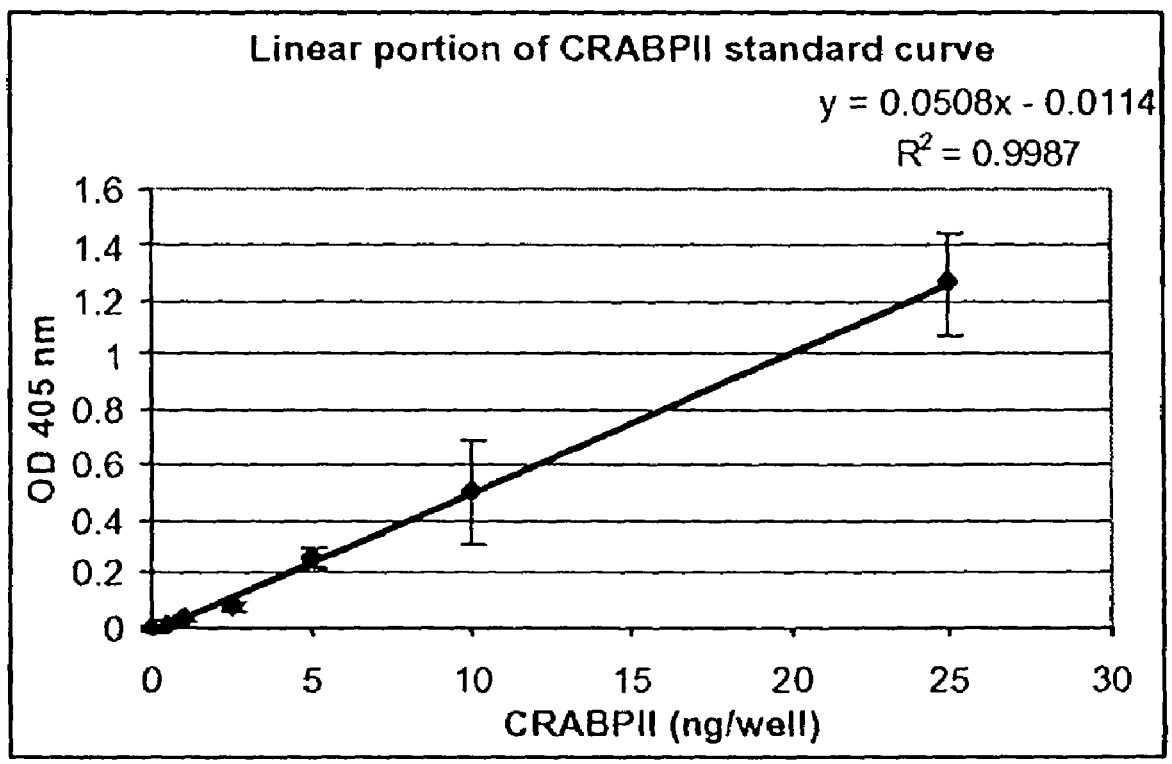
FIG. 11 is a graphic representation of the linear portion of a standard curve produced using recombinant ACRABPII as the target in an ELISA assay using an anti-ACRABPII monoclonal antibody and a secondary anti-mouse IgG antibody conjugated to horseradish peroxidase.
Figure 12:
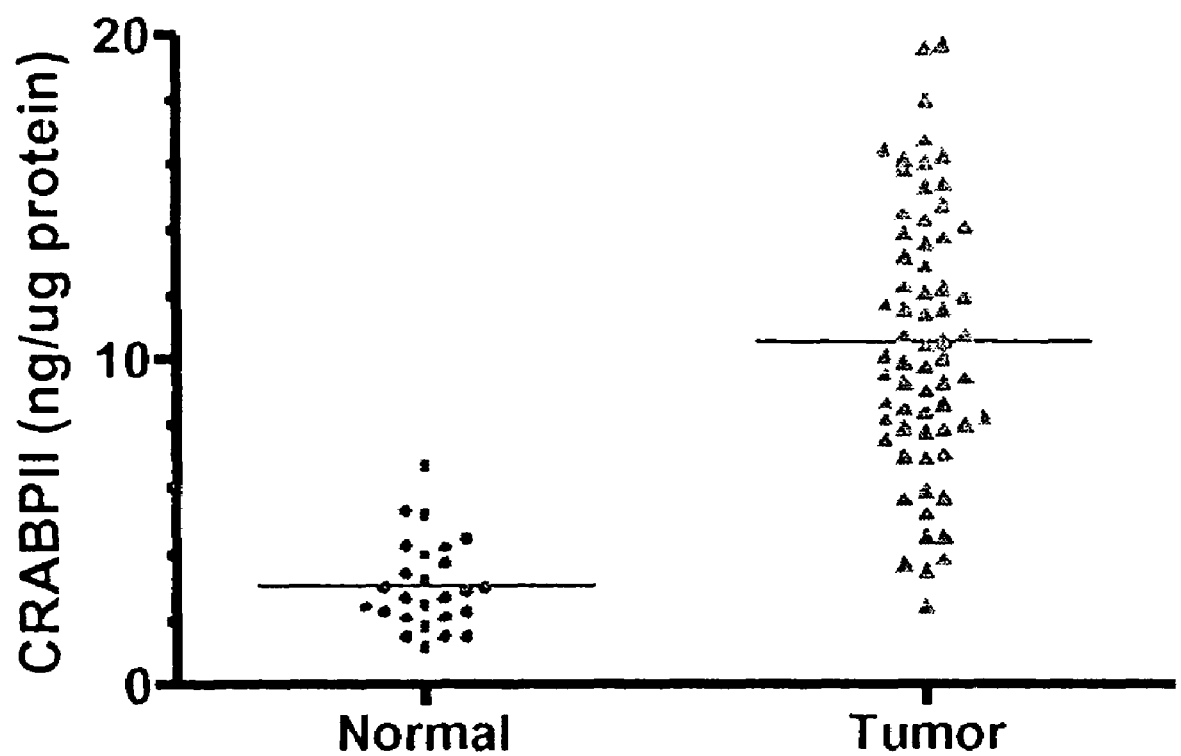
FIG. 12 is a graphic representation showing the results of an ELISA analysis comparing the levels of expression of ACRABPII in normal breast tissue subjects and breast cancer patients.
Figure 13:
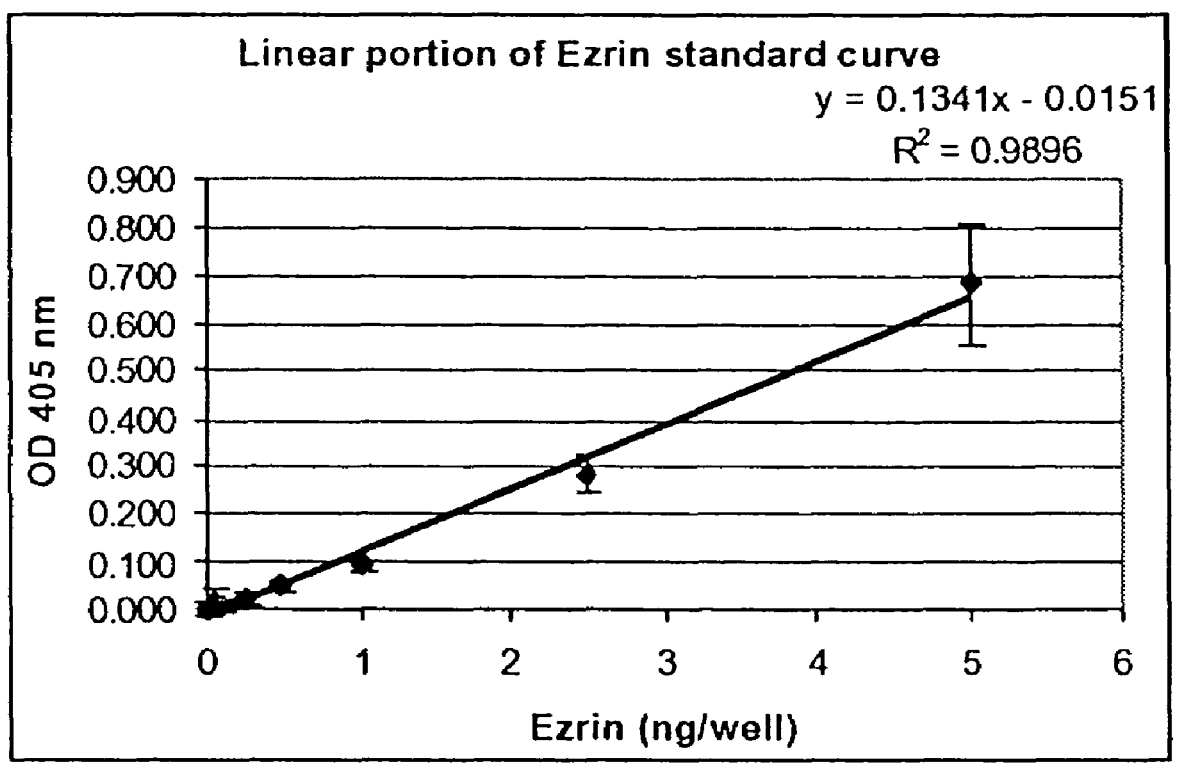
FIG. 13 is a graphic representation of the linear portion of a standard curve produced using recombinant ezrin as the target in an ELISA assay using an anti-ezrin monoclonal antibody and a secondary anti-mouse IgG antibody conjugated to horseradish peroxidase.
Figure 14:
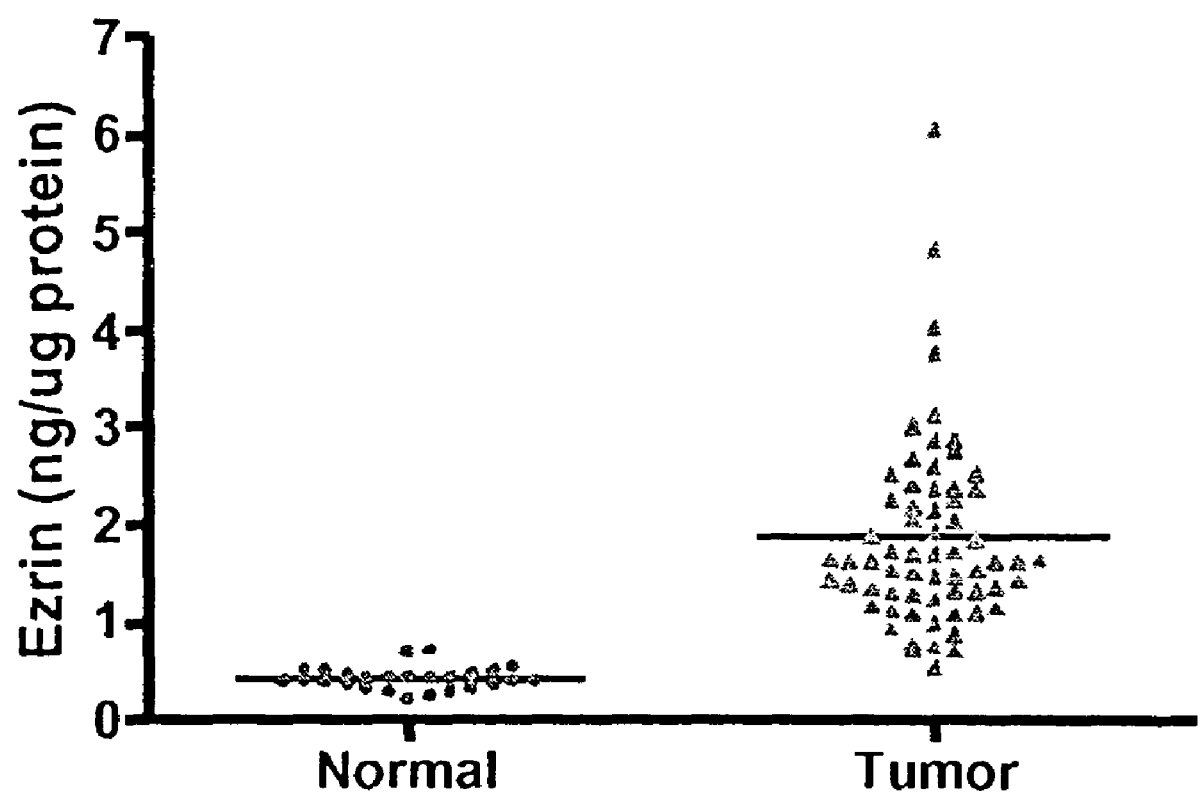
FIG. 14 is a graphic representation showing the results of an ELISA analysis comparing the levels of expression of ezrin in normal breast tissue subjects and breast cancer patients.
Figure 15:
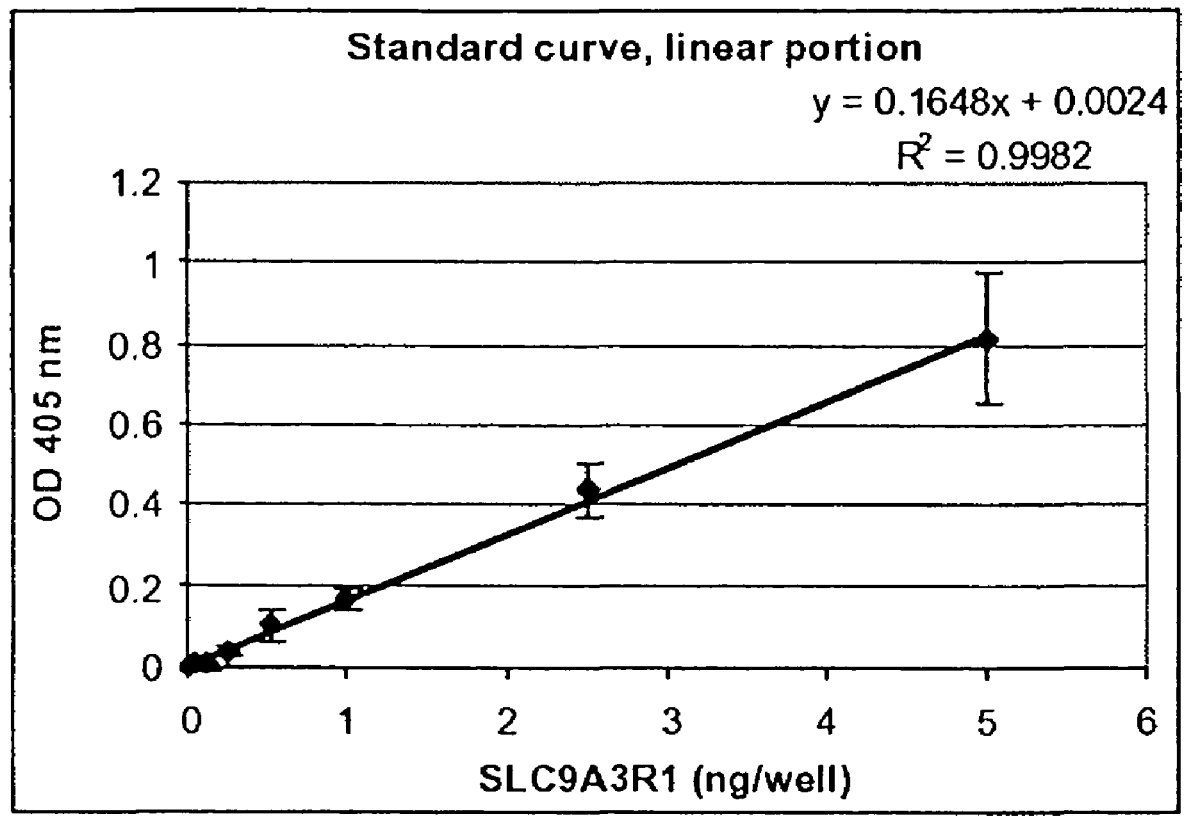
FIG. 15 is a graphic representation of the linear portion of a standard curve produced using recombinant slc9a3rl as the target in an ELISA assay using an anti-slc9a3rl monoclonal antibody and a secondary anti-mouse IgG antibody conjugated to horseradish peroxidase.

The carrier protein slc9a31 showed increased expression levels at the protein level in tumor samples as compared to normal samples (FIGS. 6A and 6B). Protein expression for slc9a31 was increased by 2.7-fold in the tumors. Western blot analysis clearly showed that few normal subjects showed similar slc9a31 protein expression to any breast cancer patient (FIG. 6A).

A summary of the protein targets analyzed in this study is shown below in Table 1.

TABLE 1

| Fold Increase Expression in Tumors | Protein marker |
|---|---|
| 3.7 | cathepsin D |
| 3.7 | ezrin |
| 7.9 | cytokeratin 19 |
| 2.7 | slc9a3rl |
| 3.4 | A-CRABP II |
| 5.2 | HER-2 |

Depending on the classifiers used, 89% to 92% of the patients were classified in their respective classes with a protein classifier composed of 4 different proteins.

Table 2 shows the performance of all classifiers for the breast training set (98 cases).

TABLE 2

| Classifiers | Two Fold Expression Increase | Three Fold Expression Increase |
|---|---|---|
| CCP | 90% | 89% |
| LDA | 91% | 89% |
| 1-NN | 92% | 89% |
| 3-NN | 91% | 88% |
| NC | 89% | 88% |
| SVM | 89% | 90% |

The 1-Nearest Neighbor (1-NN) was the best classifier method for that breast training set (Table 2). The other classifier methods used included compound covariate predictor (CCP), diagonal linear discriminant analysis (LD), 3-nearest neighbor predictor (3-NN), nearest centroid predictor (NC), and support vector machine predictor (SVM). Sensitivity toward the normal class was 88.9% with a specificity of 93%. PPV was 82.8% and NPV was 95.7%. For the tumor class, a sensitivity of 93% was calculated for the classifier method with a specificity of 88.9% and a PPV of 95.7% and a NPV of 82.8%. Percentages represent accurate tumor classification of patient when protein markers have greater than a two-fold or three-fold increase in expression in tumor tissues as compared to normal tissues.

Figure 16:
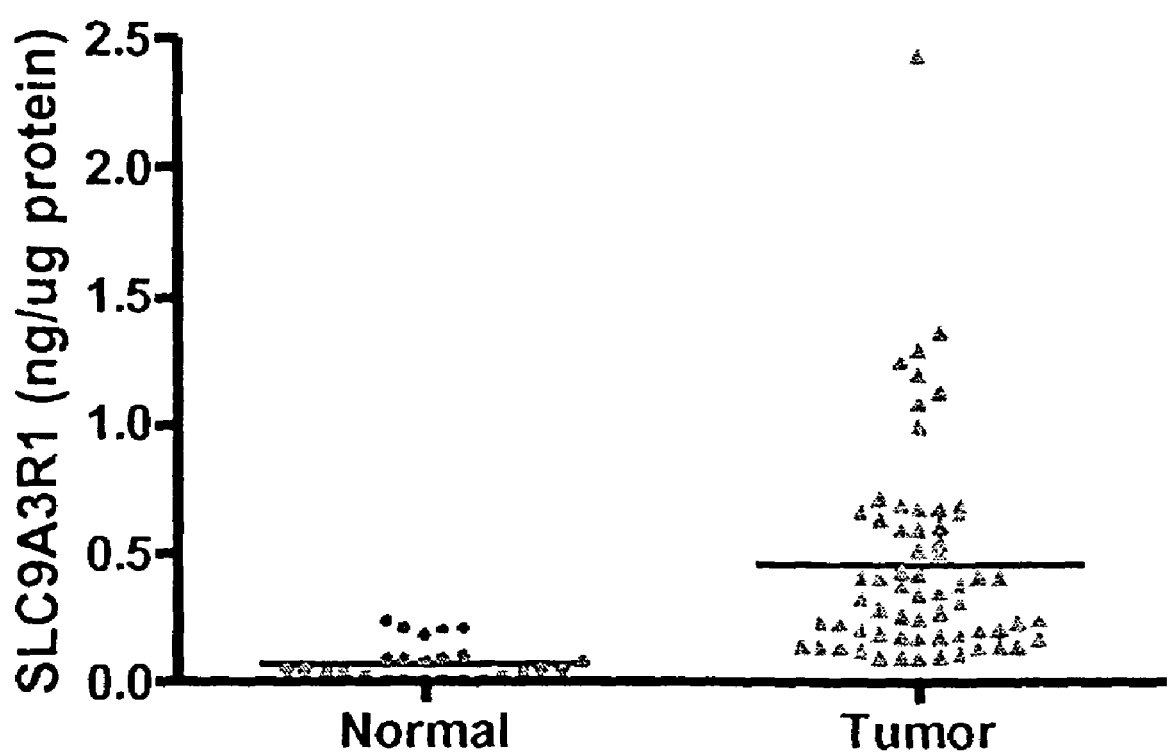
FIG. 16 is a graphic representation showing the results of an ELISA analysis comparing the levels of expression of slc9a3rl in normal breast tissue subjects and breast cancer patients.

Additional ELISA analyses confirmed that cytokeratin 19, cathepsin D, ACRABPII, and ezrin showed large differences in mean expression levels (FIGS. 8, 10, 12, 14). Scatter plots of protein expression levels in individuals showed that the tumor group generally showed higher levels of expression for cytokeratin 19, cathepsin D, ACRABPII, and ezrin than individuals associated with the normal group showed for the same proteins (FIGS. 8, 10, 12, 14). Also, slc9a3rl was expressed at higher levels in most individuals in the tumor group than in the normal group (FIG. 16). Protein expression levels were typically determined using standard curves (FIGS. 7, 9, 11, 13, 15).

EXAMPLES

Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Classification of Cell Samples Isolated from Breast Cancer Patients and Normal Breast Subjects 1. Patient Samples and Normal Samples Patient material was obtained from Asterand, Inc. (Detroit, Mich.), Clinomics Biosciences, Inc (Watervliet, N.Y.) and Biochain Institute, Inc. (Hayward, Calif.). For the breast cancer groups, only patients with greater than 70% tumor cell content in the tumor mass were included in the studies. Total RNA was extracted from snap frozen tissue samples with the Trizol Reagent kit (Gibco-BRL, Carlsbad, Calif.) using the recommended extraction procedures of Asterand, Inc., Clinomics Biosciences, Inc. or Biochain Institute, Inc. Total RNA was treated with RNA-free DNAse I (New England BioLabs, Beverly, Mass.) and purified with the RNEasy kit (Qiagen, Hilden, Germany). RNA samples were visualized on an Agilent 2100 BioAnalyzer (Agilent Technologies, Foster City, Calif.).

Each patient included in the study was screened against the same normal total RNA pool in order to compare them together. Breast normal total RNA pools were purchased from Biochain Institute, Inc. (Hayward, Calif.). The breast normal pool was composed of 20 cases. The normal breast subjects (79 cases) and the breast cancer patients (57 cases) were screened on the focused microarray in triplicate.

2. Western Blot Analysis of Protein Markers in Breast Cancer and Breast Normal Tissues For breast tissues, 30 mg of proteins from homogenates and from human breast cell lines MCF-7 and MDA-MB-231 were used. Samples were mixed with Laemmli buffer (250 mM Tris-HCl, pH 8.0, 25% (v/v) b-mercaptoethanol, 50% (v/v) glycerol, 10% (w/v) SDS, 0.005% (w/v) bromophenol blue), heated for 5 minutes at 95° C. and resolved in 12% SDS-polyacrylamide gels (SDS-PAGE). Proteins were then electro-transferred onto Hybond-ECL nitrocellulose membranes (Amersham Biosciences, Baie d'Urfé, Canada) for 90 minutes at 100 volts at room temperature. Membranes were blocked for 1 hour at room temperature in blocking solution (PBS containing 5% fat-free dry milk). Membranes were washed with PBS and incubated with the primary antibodies at the appropriate dilutions in blocking solution containing 0.02% sodium azide for 2 hours at room temperature. PBS washing was performed, and the membranes were subsequently incubated for 1 hour at room temperature with secondary anti-mouse, anti-rabbit or anti-goat antibodies labeled with horseradish peroxydase (Bio-Rad, Mississauga, Canada) diluted 1/3000 in PBS. Chemiluminescence detection was performed using the SuperSignal West Pico Chemiluminescent Substrate (Pierce, Rockford, Ill., USA) following the manufacturer's recommendations.

The results of expression analyses for the protein markers are shown in FIGS. 1-6.

3. ELISA Analysis of Protein Markers in Breast Cancer and Breast Normal Tissues

To quantify the amount of each target of interest and to confirm the results obtained by Western blot, an ELISA technique was performed on breast samples for all protein markers being analyzed in the present study. These markers included cytokeratin 19, ezrin, cathepsin D, A-CRABP II, slc9a3rl, and HER-2. Prior to screening all samples, an optimization of the conditions was performed using normal and tumor samples to determined the linearity of the assay (dose-dependant curve, time of development of the assay) for each target to be analyzed in this assay. Once conditions were optimized, 96-well plates (Maxisorp plates, NUNC, (Rochester, N.Y., USA)) were coated with the appropriate amount of samples and incubated overnight at 4° C. Wells were washed 3 times with PBS and then blocked with 3% bovine serum albumin (BSA)/PBS for 1 hour at room temperature. Primary antibodies (40 ng/well) were added to the wells and incubated for 2 hours at room temperature. Plates were washed 3 times with PBS and the secondary anti-mouse, anti-rabbit or anti-goat antibodies labeled with horseradish peroxidase (Bio-Rad, Mississauga, Canada), diluted 1:3000 in 3% BSA/PBS, were incubated for 1 hour at room temperature. Wells were washed 3 times with PBS and developed with 2,2'-azino-bis(3-ethylbenzthiazoline-6-sulfonic acid) (ABTS) as the substrate (Sigma Corp., St. Louis, Mo.).

The intensity of the signal was assessed by reading the plates at a 405 nm wavelength using a microplate reader. For each of the target, a standard curve was established with a recombinant or purified protein at the same time to quantify the target in each sample. Results were expressed as concentrations of a target in 1 µg of total protein extract. All samples were quantified in the same assay. Differences among normal and tumor groups were analyzed using Student's two-tailed t test with significance level defined as $P<0.05$. ELISA results are shown in FIGS. 1-6 as scatter plots showing the levels of protein expression for each protein marker. Results are shown as µg/mg of protein marker in each normal subject versus µg/mg of protein marker in each breast cancer patient.

4. Classification of Breast Cancer Patients Using Classification Algorithms

Class prediction analyses were performed using the BRB ArrayTools developed by Dr. Richard Simon (NIH/NCI) and Amy Peng. Briefly, class prediction analyses were done on the results obtained for each patient in the study. Patients were divided into two classes following their malignancy: normal class and tumor class. These classes became the training sets by which patients were compared for purposes of classification. The classification algorithms used the expression data from the training sets to make all patient classifications during the tests. Class determination was done based on the clinical data associated to each patient. There were six different classification algorithms used in the studies: compound covariate predictor, diagonal linear discriminant analysis, nearest neighbor predictor (1-NN and 3-NN), nearest centroid predictor and support vector machine predictor. Those analyses permitted the development of a multi-gene classifier to predict the class for a new sample and estimate the misclassification rates. Cross-validation of the class prediction classifiers were done by the leave one-out study and permutation tests (n=2000) were conducted to address significance of the cross-validation test error rate.

To evaluate the performances of these ELISA and Western Blot assays in predicting accurately a diagnostic for breast cancer, the sensitivity, the specificity, the positive predicting value (PPV) and the negative predicting value (NPV) were determined for multiple protein markers. ELISA breast training set data was composed of 98 cases divided as follow: 27 normal and 71 tumors. The results are shown in Table 3.

TABLE 3

| Markers with Increased Expression* | Patients with Increased Expression** | Percent of Total Patients |
|---|---|---|
| 5/5 | 43 | 61 |
| 4/5 | 20 | 28 |
| 3/5 | 2 | 3 |
| 2/5 | 5 | 7 |
| 1/5 | 0 | 0 |
| 0/5 | 1 | 1 |
| Total | 71 | 100 |

*total markers with increased expression in the sample
**the number of patients having tumors showing that number of markers increased in expression A high accuracy can be obtained when we compare ELISA protein profile obtained for both breast groups. These parameters were determined by two different methods: 1) by visual assessment of the signal from Western blot data, and 2) by analyzing the ELISA data by using the software BRB-array Tools designed for microarray data analysis (Table 3).

This software used 6 different algorithms to make the predictions. Table 3 shows that the assays were 92% sensitive at identifying a breast neoplasm, while the assays were 85% specific in identifying a tumor.

Example 2

Classification of Cell Samples Isolated from Breast Cancer Patients and Normal Breast Subjects 1. Patient Samples and Normal Samples Patient material was obtained from Asterand, Inc. (Detroit, Mich.), Clinomics Biosciences, Inc (Watervliet, N.Y.) and Biochain Institute, Inc. (Hayward, Calif.). Each patient included in the study was screened against the same normal total RNA pool in order to compare them together. The tumor pool comprised 65 samples. The breast normal pool was composed of 26 samples. FIG. 17 shows the patient profiles for individuals diagnosed with breast cancer and individuals belonging to the normal tissue group.

2. ELISA Analysis of Protein Markers in Breast Cancer and Breast Normal Tissues

Human breast tissues (20-50 mg) were homogenized using a Polytron PT10-35 (Brinkmann, Mississauga, Canada) for 30 seconds at speed setting of 4 in the presence of 300 µl of CelLytic MT Extraction Reagent (Sigma Corp., St. Louis, Mo.) and a cocktail of protease inhibitors from Roche Corp. (Laval, Qc, Canada). Protein concentration was determined using the DC Protein Assay Kit (Bio-Rad Laboratories, Mississauga, Calif.) and measuring the absorbance of the reaction on an Ultrospec 2000 Spectrophotometer (Pharmacia Biotech, Cambridge, UK) at $A_{750}$.

To quantify the amount of each target of interest, an ELISA technique was performed on breast samples for all protein markers being analyzed in the present study. These markers included cathepsin D, cytokeratin 19, ACRABPII, ezrin, and slc9a3rl. Prior to screening all samples, an optimization of the conditions was performed using normal and tumor samples to determined the linearity of the assay (dose-dependant curve, time of development of the assay) for each target to be analyzed in this assay. Once conditions were optimized, 96-well plates ((Maxisorp plates, NUNC, (Rochester, N.Y., USA)) were used for all ELISA studies. Wells were coated with 1 µg of each sample and incubated overnight at 4° C. Wells were washed 3 times with PBS and then blocked with 3% bovine serum albumin (BSA)/PBS for 1 hour at room temperature. The plates were then manually washed 3 times with PBS (Sigma Corp., St. Louis, Mo.), and blocked with 3% bovine serum albumin in PBS for 1 hour at room temperature. Monoclonal, primary antibodies were obtained from mouse and goat hybridomas. Primary antibodies were added to the wells at a concentration of 40 ng/well for cytokeratin 19, ACRABPII, ezrin, and slc9a3rl. Primary antibody directed against cathepsin D was added at a 1:100 ratio. The reaction mixtures were incubated for 2 hours at room temperature. Plates were washed 3 times with PBS and the secondary anti-mouse, anti-rabbit or anti-goat antibodies labeled with horseradish peroxidase (Bio-Rad, Mississauga, Canada), diluted 1:3000 in 3% BSA/PBS, were incubated for 1 hour at room temperature. Wells were washed 3 times with PBS and developed with 2,2'-azino-bis(3-ethylbenzthiazoline-6-sulfonic acid) (ABTS) as the substrate (Sigma Corp., St. Louis, Mo.). A standard curves were performed with the study samples. A negative control was also used. All samples were performed in triplicate.

The intensity of the signal was assessed by reading the plates at a 405 nm wavelength using a microplate reader. For each of the target, a standard curve was established with a recombinant or purified protein at the same time to quantify the target in each sample. Results were expressed as concentrations of a target in 1 µg of total protein extract. All samples were quantified in the same assay. Differences among normal and tumor groups were analyzed using Student's two-tailed t test with significance level defined as P<0.05. ELISA results are shown in FIGS. 1-6 as scatter plots showing the levels of protein expression for each protein marker. Results are shown as µg/mg of protein marker in each normal subject versus µg/mg of protein marker in each breast cancer patient.

3. Classification of Breast Cancer Patients Using Classification Algorithms

Class prediction analyses were performed using the BRB ArrayTools developed by Dr. Richard Simon (NIH/NCI) and Amy Peng. Briefly, class prediction analyses were done on the results obtained for each patient in the study. Patients were divided into two classes following their malignancy: normal class and tumor class. These classes became the training sets by which patients were compared for purposes of classification. The classification algorithms used the expression data from the training sets to make all patient classifications during the tests. Class determination was done based on the clinical data associated to each patient. There were six different classification algorithms used in the studies: compound covariate predictor, diagonal linear discriminant analysis, nearest neighbor predictor (1-NN and 3-NN), nearest centroid predictor and support vector machine predictor. Those analyses permitted the development of a multi-gene classifier to predict the class for a new sample and estimate the misclassification rates. Cross-validation of the class prediction classifiers were done by the leave one-out study and permutation tests (n=2000) were conducted to address significance of the cross-validation test error rate.

To evaluate the performances of the ELISA assays in predicting accurately a diagnostic for breast cancer, the sensitivity, the specificity, the positive predicting value (PPV) and the negative predicting value (NPV) were determined for multiple protein markers. A breast training set data was composed of 91 cases divided as follow: 26 normal and 65 tumors.

A high accuracy was obtained when we compare ELISA protein profile obtained for both breast groups. All results were analyzed by using a Student's two-tailed t test with the significance level defined as P<0.05 and/or the BRB-array Tools software designed for microarray data analysis. Cut-off values used for the ELISA data analysis were calculated for each target as the mean of the normal tissues plus 2 standard deviation values. A cut-off value is used to determine what level of expression for a particular marker would qualify the sample as being a tumor. Any level of expression above the cut-off value would represent a tumor diagnosis, while levels of expression below the cut-off value would indicate that the tissues were normal.

4. Results.

The markers used in the present study showed increased levels of expression in tumor tissue samples as compared to normal tissue samples. Breast tumor samples showed between a 3.5-fold and 8.3-fold increase in the level of expression of the biomarkers analyzed in this study (Table 4).

TABLE 4

| Protein Markers | Fold Increase In Tumor |
|---|---|
| Cytokeratin 19 | 8.3 |
| Slc9a3r1 | 6.6 |
| Cathepsin D | 3.9 |
| Ezrin | 3.6 |
| ACRABPII | 3.5 |

The amount of protein expressed in normal and tumor tissues was also determined by ELISA analysis using standard curves developed for each protein (FIGS. 7, 9, 11, 13, 15). The results are shown in Table 5.

TABLE 5

| | Quantity Expressed Protein (ng) | |
|---|---|---|
| Protein Marker | Normal Tissues | Breast Tumor Tissues |
| Cytokeratin 19 | 1.92 ± 1.85 | 16.01 ± 9.55 |
| Slc9a3r1 | 0.069 ± 0.073 | 0.457 ± 0.413 |
| Cathepsin D | 0.82 ± 0.54 | 3.18 ± 1.08 |
| Ezrin | 0.417 ± 0.121 | 1.506 ± 0.727 |
| ACRABPII | 3.02 ± 1.37 | 10.60 ± 4.09 |

The level of expression of each protein was also analyzed in individual samples and plotted to determine the average level of expression of each protein within normal and tumor samples as well as the differences in levels of expression between individuals in the same group. Cytokeratin 19, cathepsin D, ACRABPII, and ezrin showed large differences in mean expression levels (FIGS. 8, 10, 12, 14). In addition, individuals in the tumor group generally showed higher levels of expression for cytokeratin 19, cathepsin D, ACRABPII, and ezrin than individuals associated with the normal group (FIGS. 8, 10, 12, 14). Also, slc9a3r1 was expressed at higher levels in most individuals in the tumor group than in the normal group (FIG. 16). The mean level of expression for the tumor group was also higher than the level of expression for slc9a3r1 in the normal group, though not as high as the other proteins (FIG. 16). Therefore, the levels of expression for these proteins were all higher for the tumor group as compared to the normal group.

Also, the ELISA data was analyzed to determine the ability of the chosen markers to discriminate between tumors and normal tissues. The sensitivity of the test for patients with breast cancer was 95.4%. As used herein, "sensitivity" means the ability of an assay to detect and properly identify a tumor. The test was also highly specific, showing 100% specificity for individuals with no evidence of cancer. As used herein, the term "specificity" means the ability of a particular marker or combination of markers to properly identify normal tissues without falsely identifying normal tissues as being tumors. Furthermore, the accuracy of the assay was 96.7% after comparing the results of the assay to the determinations made by a pathologist. This indicates that the markers are capable of identifying tumors, while not producing false positives.

The levels of expression for individual tumor and normal samples were also analyzed to determine whether individual samples are above or below the expression cut-off level described above. The cut-off values are shown in Table 6.

TABLE 6

| Protein Marker | Cut-Off Value |
|---|---|
| Cytokeratin 19 | 5.63 |
| Slc9a3r1 | 1.89 |
| Cathepsin D | 5.75 |
| Ezrin | 0.659 |
| ACRABPII | 0.216 |

The levels of expression of each marker in normal tissue samples and tumor samples showed differential expression of the protein markers. The tables show that normal tissue samples have lower levels of expression in most cases, and that few samples are above the cut off described above. Furthermore, most normal tissues have levels of expression that is lower than the cut-off value for the marker, which indicates that the tissue is normal. The reverse is true for tumor tissues, most of which have levels of expression for all markers that is greater than the cut-off values for these markers. Thus, the levels of expression of each marker provides specific and sensitive diagnoses for cancer. It is also apparent that a combination of these markers would provide a specific and sensitive tool for diagnosing breast tumors.

EQUIVALENTS

Those skilled in the art will recognize, or be able to ascertain, using no more than routine experimentation, numerous equivalents to the specific compositions and procedures described herein. Such equivalents are considered to be within the scope of this invention, and are covered by the following claims.

The invention claimed is:

1. A method of diagnosing breast cancer in the subject, comprising:
   a) selecting protein makers, wherein the protein markers are the combination of cytokeratin 19, cathepsin D, ezrin, and slc9a3r1;
   b) detecting a level of expression of the selected protein markers in a biological fluid sample isolated from the subject by contacting the biological fluid sample with a targeting agent specific for a protein marker in the combination of the selected protein markers;
   c) detecting a level of expression of the selected protein markers in a control biological fluid sample by contacting the control sample with the targeting agent specific for a protein marker in the combination of the selected protein markers; and d) comparing the levels of expression of the selected protein markers in the biological fluid sample to the levels of expression of the same protein markers in the control sample, wherein the presence of breast cancer is indicated if the level of expression of the selected protein markers in the biological fluid sample is greater than the level of expression for the selected protein markers in the control sample.

2. The method of claim 1, further comprises detecting a level of expression of HER-2.

3. The method of claim 1, wherein the level of expression of protein markers is detected by protein capture probes attached to a solid support.

4. The method of claim 1, wherein the subject is a human.

5. The method of claim 1, wherein the biological fluid sample is selected from the group consisting of blood, bile, serum, sweat, urine, mucosal secretions, saliva, seminal fluid, cerebrospinal fluid, tears, and sebaceous secretions.

6. The method claim 5, wherein the biological fluid sample comprises blood or serum.

* * * * *